US006608035B1

(12) United States Patent
Agrawal et al.

(10) Patent No.: US 6,608,035 B1
(45) Date of Patent: Aug. 19, 2003

(54) METHOD OF DOWN-REGULATING GENE EXPRESSION

(75) Inventors: Sudhir Agrawal, Shrewsbury, MA (US); Robert B. Diasio, Birmingham, AL (US); Ruiwen Zhang, Birmingham, AL (US)

(73) Assignee: Hybridon, Inc., Cambridge, MA (US)

( * ) Notice: Subject to any disclaimer, the term of this patent is extended or adjusted under 35 U.S.C. 154(b) by 80 days.

(21) Appl. No.: 09/587,934

(22) Filed: Jun. 6, 2000

Related U.S. Application Data

(63) Continuation of application No. 08/758,005, filed on Nov. 27, 1996, now abandoned, which is a continuation-in-part of application No. 08/709,910, filed on Sep. 9, 1996, now abandoned, which is a continuation-in-part of application No. 08/328,520, filed on Oct. 25, 1994, now Pat. No. 5,591,721.

(51) Int. Cl.$^7$ .......................... A01N 43/04; C12Q 1/68; C12P 19/34; C07H 21/02; C07H 21/04

(52) U.S. Cl. .......................... 514/44; 435/6; 435/91.1; 536/23.1; 536/24.5

(58) Field of Search .................... 435/6, 91.1, 91.5, 435/455, 375; 935/34; 514/44; 536/23.1, 24.5, 25.3

(56) References Cited

U.S. PATENT DOCUMENTS

| | | | |
|---|---|---|---|
| 4,309,404 A | | 1/1982 | DeNeale et al. |
| 4,309,406 A | | 1/1982 | Guley et al. |
| 4,556,552 A | | 12/1985 | Porter et al. |
| 4,704,295 A | | 11/1987 | Porter et al. |
| 5,149,797 A | | 9/1992 | Pederson et al. |
| 5,220,007 A | | 6/1993 | Pederson et al. |
| 5,248,670 A | | 9/1993 | Draper et al. |
| 5,271,941 A | | 12/1993 | Cho-Chung |
| 5,403,709 A | | 4/1995 | Agrawal et al. |
| 5,442,049 A | | 8/1995 | Anderson et al. |
| 5,470,967 A | | 11/1995 | Huie et al. |
| 5,510,239 A | * | 4/1996 | Baracchini et al. ............ 435/6 |
| 5,514,577 A | | 5/1996 | Draper et al. |
| 5,578,716 A | | 11/1996 | Szyf et al. |
| 5,591,721 A | | 1/1997 | Agrawal et al. |
| 5,612,212 A | | 3/1997 | Gewirtz |
| 5,652,355 A | | 7/1997 | Metelev et al. |
| 5,969,117 A | | 10/1999 | Agrawal |
| 6,143,881 A | | 11/2000 | Metelev et al. |

FOREIGN PATENT DOCUMENTS

| | | |
|---|---|---|
| WO | WO 94/02498 | 2/1994 |
| WO | WO 94/15619 | 7/1994 |
| WO | WO94/23028 | 10/1994 |
| WO | WO96/12497 | 5/1996 |
| WO | WO97/11171 | 3/1997 |

OTHER PUBLICATIONS

Schofield et al. Brit. Med. Bull. vol. 51, No. 1, pp. 56–71, 1995.*
Crystal, R.G. Science. vol. 270, pp. 404–410, 1995.*
Friedmann, T. Scientific American. Jun. vol., pp. 96–101, 1997.*
Verma et al. Nature, vol. 389, pp. 239–242, 1997.*
Branch, A. Trends in Biochem. Sci., vol. 23, pp. 45–50, 1998.*
Crooke, S.T. Antisense Res. and Application. Chapter 1, pp. 1–50, published by Springer–Verlag, 1998.*
Uhlmann et al. Chemical Reviews, vol. 90, No. 4, pp. 544–579, 1990.*
Wickstrom (1986) *J. Biochem. Biophys. Meth.* 13:97–102.
Inoue et al. (1987) *FEBS Lett.* 215:237–250.
Agrawal et al. (1988) *Proc. Natl. Acad. Sci. (USA)* 85:7079–7083.
Agrawal et al. (1989) *Proc. Natl. Acad. Sci. (USA)* 86:7790–7794.
Furdon et al. (1989) *Nucleic Acids Res.* 17:9193–9204.
Quartin et al. (1989) *Nucleic Acids Res.* 17:7523–7562.
Agrawal et al. (1990) *Proc. Natl. Acad. Sci. (USA)* 87:1401–1405.
Agrawal et al. (1991) *Proc. Natl. Acad. Sci. (USA)* 88:7595–7599.
Iversen (1991) *Anti–Cancer Drug Design* 6:531–538.
Agrawal (1992) *Trends in Biotech.* 10:152–158.
Iversen (1994) *Antisense Res. Devel.* 4:43–52.
Sands (1994) *Mol. Pharm.* 45:932–943.
Hughes et al. (1995) *Pharmaceutical Research* 12:817–824.
Milligan et al. (1993) *J. Med. Chem.* 36:1923–1937.
Stein et al. (1993) *Science* 261:1004–1012.
Tseng et al. (1994) *Cancer Gene Therapy* 1:65–71.
Shibahara et al. (1989) *Nucleic Acids Research* 15:4403–4415.
Shibahara et al. (1989) *Nucleic Acids Research* 17:239–252.
Takashima et al. (1993) *Proc. Natl. Acad. Sci.* 90:7789–7793.
Rapaport et al. (1992) *Proc. Natl. Acad. Sci.* 89:8577–8580.
Uhlmann et al. (1990) *Chem. Rev.* 90:543–584.
Kawasaki et al. (1993) *J. Med. Chem.* 36:831–841.
Agrawal et al. (1995) *Biochemical Pharmacology* 50:571–576.
Wickstrom (1992) *TIBITECH* 10:281–287.
Tidd et al. (1989) *British Journal of Cancer* 60:343–350.
Agrawal, *Antisense Therapeutics*, (Sudhir Agrawal, ed.), p. V (1996).
Craig et al., *Exp. Opin. Ther. Patents* 7:1175–1182 (1997).

(List continued on next page.)

*Primary Examiner*—Ram R. Shukla
*Assistant Examiner*—Jane Zara
(74) *Attorney, Agent, or Firm*—Hale and Dorr LLP

(57) ABSTRACT

Disclosed is a method of down-regulating the expression of a gene in an animal, wherein a pharmacological formulation comprising a chimeric oligonucleotide complementary to the gene is orally administered to an animal. The oligonucleotide administered has at least one phosphorothioate internucleotide linkage and at least one alkylphosphonate, phosphorodithioate, alkylphosphonothioate, phosphoramidate, phosphoramidite, phosphate ester, carbamate, carbonate, phosphate triester, acetamidate, or carboxymethyl ester internucleotide linkage.

2 Claims, 12 Drawing Sheets

OTHER PUBLICATIONS

Galderisi et al., "Antisense oligonucleotides as therapeutic agents." *J. Cell. Physiol.*, vol. 181, pp. 251–257 (1999).

Isis Pharmaceuticals—Press Release 060500, Jun. 5 (2000).

Tortora et al., "Oral antisense that targets protein kinase A cooperates with taxol and inhibits tumor growth, angiogenesis, and growth factor production." *Clin Cancer Res.* vol. 6, No. 6, pp. 2506–2512 (2000).

Wang et al., "Antitumor activity and pharmacokinetics of a mixed–backbone antisense oligonucleotide targeted to the Rlalpha subunit of protein kinase A after oral administration." *Proc Natl Acad Sci U S A.*, vol. 96, No. 24, pp. 13989–13994 (1999).

Zamecnik, "History of Antisense Oligonucleotides" *Antisense Therapeutics*, (Sudhir Agrawal, ed.), pp. 1–11 (1996).

Shibahara et al, *Nucleic Acids Research* 15: 4403–4415 (1987).

Zon, *Pharm. Res* 5(9): 539–49 (1988).

Ceruzzi et al, *Nucleosides and Nucleotides* 8 (5&6): 815–8 (1989).

Zendegui et al, *Nucleic Acids Research* 20: 307–314 (1992).

Bayever et al, *Antisense Res. and Dev.* 3: 383–90 (1993).

Zhao et al, *Antisense Res. and Dev.* 3: 53–66 (1993).

Boutorine et al, *Biochimie* 76: 23–32 (1994).

Metelev et al, *Bioorganic & Medicinal Chemistry Letters*, 4: 2929–2934 (1994).

Sonveaux, "*Protecting Groups in Oligonucleotide Synthesis*", in *Methods in Molecular Biology* (Agrawal ed.) 26:1–71 (1994).

Martin, P . *Helvetica Chimica Acta*, 78: 486–504 (1995) Abstract Only.

Isis Pharmaceuticals, Inc., *Antisense 97: Targeting the Molecular Basis of Disease*, Nature Biotechnology Conference, May 1–2 1997.

International Business Communications, *IBC,'s Fourth Annual International Sysmposium on Oligonucleotides and Gene Therapy–Based Antisense Therapeutics with New Applications for Genomics*, Feb. 6–7 1997.

Agrawal, "Functionalization of Oligonucleotides with Amino Groups and Attachment of Amino Specific Reporter Groups", Methods in Molecular Biology, vol. 26: Protocols for Oligonucleotide Conjugates, pp. 93–120, 1994.

Agrawal, "Preface", *Methods in Molecular Medicine: Antisense Therapeutics* (Agrawal Ed.), Humana Press, pp. v–vii, 1996.

Agwaral, et al., "Comparative Pharmacokinetics of Antisense Oligonucleotides", *Methods in Molecular Medicine: Antisense Therapeutics* (Agrawal Ed.), Humana Press, pp. 247–270, 1996.

Agrawal, "In Vivo Pharmacokinetics of Oligonucleotides" *Applied Antisense Oligonucleotide Technology* (Stein and Kried Ed.), Wiley–Liss, pp. 365–385, 1998.

Inoue, et al., "Sequence–dependent Hydrolysis of RNA using Modified Oligonucleotide Splints and R Nase H", FEBS Letters, vol. 215, No. 2, pp. 327–330, May 1987.

Monia et al, "Antitumor Activity of a Phosphorothioate Antisense Oligodeoxynucleotide Targeted Against C–raf Kinase", Nature Medicine, vol. 2, No. 6, pp. 668–675, Jun. 1996.

Vlassov et al., "Penetration of Oligonucleotides into Mouse Organism through Mucosa and Skin", FEBS Letters, vol. 327, No. 3, pp. 271–274, Aug. 1993.

Vlassov et al., "In Vivo Pharmacokinetics of Oligonucleotides Following Administration by Different Routes", *Delivery Strategies for Antisense Oligonucleotide Therapeutics* (Akhtar Ed.), CRC Press, pp. 71–83, 1995.

* cited by examiner

SEQUENCE LISTING

```
<160> NUMBER OF SEQ ID NOS: 21

<210> SEQ ID NO 1
<211> LENGTH: 25
<212> TYPE: DNA
<213> ORGANISM: Artificial Sequence
<220> FEATURE:
<223> OTHER INFORMATION: Antisense
      DNA/RNA
```

<400> SEQUENCE: 1
ctctcgcacc catctctctc cttcu                                    25

<210> SEQ ID NO 2
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 2
ctctcgcacc catctctctc ctucu                                    25

<210> SEQ ID NO 3
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 3
ctctcgcacc catctctctc cuucu                                    25

<210> SEQ ID NO 4
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 4
ctctcgcacc catctcucuc cuucu                                    25

<210> SEQ ID NO 5
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 5
ctctcgcacc caucucucuc cuucu                                    25

<210> SEQ ID NO 6
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 6
ctctcgcacc caucucucuc cuucu                                    25

<210> SEQ ID NO 7
<211> LENGTH: 25
<212> TYPE: DNA
<213> ORGANISM: Artificial Sequence
<220> FEATURE:
<223> OTHER INFORMATION: Antisense
      DNA/RNA

```
<400> SEQUENCE: 7
ctctcgcacc caucucucuc cuucu                                              25

<210> SEQ ID NO 8
<211> LENGTH: 25
<212> TYPE: RNA
<213> ORGANISM: Artificial Sequence
<220> FEATURE:
<223> OTHER INFORMATION: Antisense

<400> SEQUENCE: 8
cucucgcacc caucucucuc cuucu                                              25

<210> SEQ ID NO 9
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 9
cuctcgcacc catctctctc cttcu                                              25

<210> SEQ ID NO 10
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 10
cucucgcacc catctctctc cuucu                                              25

<210> SEQ ID NO 11
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 11
cucucgcacc catctcucuc cuucu                                              25

<210> SEQ ID NO 12
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 12
cucucgcacc caucucucuc cuucu                                              25

<210> SEQ ID NO 13
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 13
```
cucucgcacc catctctcuc cuucu                                    25

<210> SEQ ID NO 14
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 14
cucucgcacc cauctctctc cuucu                                    25

<210> SEQ ID NO 15
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 15
cucucgcacc catctctctc cuucu                                    25

<210> SEQ ID NO 16
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 16
cuctcgcacc caucucucuc cuucu                                    25

<210> SEQ ID NO 17
<211> LENGTH: 25
<212> TYPE: DNA
<213> ORGANISM: Artificial Sequence
<220> FEATURE:
<223> OTHER INFORMATION: Antisense
      DNA/RNA

<400> SEQUENCE: 17
cuctcgcacc catctctcuc cuucu                                    25

<210> SEQ ID NO 18
<211> LENGTH: 25
<212> TYPE: DNA
<213> ORGANISM: Artificial Sequence
<220> FEATURE:
<223> OTHER INFORMATION: Antisense

<400> SEQUENCE: 18
ctctcgcacc catctctctc cttct                                    25

<210> SEQ ID NO 19
<211> LENGTH: 22
<212> TYPE: DNA
<213> ORGANISM: Artificial Sequence
<220> FEATURE:
<223> OTHER INFORMATION: Antisense

<400> SEQUENCE: 19
ctctcgcacc catctctctc ct                                       22

-continued

```
<210> SEQ ID NO 20
<211> LENGTH: 18
<212> TYPE: DNA
<213> ORGANISM: Artificial Sequence
<220> FEATURE:
<223> OTHER INFORMATION: Antisense
      DNA/RNA

<400> SEQUENCE: 20
gcgugcctcc tcacuggc                                               18

<210> SEQ ID NO 21
<211> LENGTH: 18
<212> TYPE: DNA
<213> ORGANISM: Artificial Sequence
<220> FEATURE:
<223> OTHER INFORMATION: Mismatched Control
      DNA/RNA

<400> SEQUENCE: 21
gcaugcatcc gcacaggc                                               18
```

METHOD OF DOWN-REGULATING GENE EXPRESSION

CROSS-REFERENCE TO RELATED APPLICATIONS

This application is a continuation of copending patent application Ser. No. 08/758,005, filed Nov. 27, 1996, now abandoned which is a continuation-in-part of patent application Ser. No. 08/709,910, filed Sep. 9, 1996, now abandoned, which is a continuation-in-part of patent application Ser. No. 08/328,520, filed Oct. 25, 1994, which issued as U.S. Pat. No. 5,591,721.

BACKGROUND OF THE INVENTION

The present invention relates to the control of gene expression. More particularly, this invention relates to the use of synthetic, modified oligonucleotides to down-regulate the expression of a gene in an animal.

The potential for the development of an antisense oligonucleotide therapeutic approach was first suggested in three articles published in 1977 and 1978. Paterson et al. (*Proc. Natl. Acad Sci.* (USA) (1977) 74:4370–4374) discloses that cell-free translation of mRNA can be inhibited by the binding of an oligonucleotide complementary to the mRNA. Zamecnik et al. (*Proc. Natl. Acad. Sci.* (USA) (1978) 75:280–284 and 285–288) discloses that a 13mer synthetic oligonucleotide that is complementary to a part of the Rous sarcoma virus (RSV) genome inhibits RSV replication in infected chicken fibroblasts and inhibits RSV-mediated transformation of primary chick fibroblasts into malignant sarcoma cells.

These early indications that synthetic oligonucleotides can be used to inhibit virus propagation and neoplasia have been followed by the use of synthetic oligonucleotides to inhibit a wide variety of viruses, such as HIV (see, e.g., U.S. Pat. No. 4,806,463); influenza (see, e.g., Leiter et al. (1990) (*Proc. Natl. Acad. Sci.* (USA) 87:3430–3434); vesicular stomatitis virus (see, e.g., Agris et al. (1986) *Biochem.* 25:6268–6275); herpes simplex (see, e.g., Gao et al. (1990) *Antimicrob. Agents Chem.* 34:808–812); SV40 (see, e.g., Birg et al. (1990) (*Nucleic Acids Res.* 18:2901–2908); and human papilloma virus (see, e.g., Storey et al. (1991) (*Nucleic Acids Res.* 19:4109–4114). The use of synthetic oligonucleotides and their analogs as antiviral agents has recently been extensively reviewed by Agrawal (*Trends in Biotech.* (1992) 10:152–158).

In addition, synthetic oligonucleotides have been used to inhibit a variety of non-viral pathogens, as well as to selectively inhibit the expression of certain cellular genes. Thus, the utility of synthetic oligonucleotides as agents to inhibit virus propagation, propagation of non-viral, pathogens and selective expression of cellular genes has been well established.

Improved oligonucleotides have more recently been developed that have greater efficacy in inhibiting such viruses, pathogens and selective gene expression. Some of these oligonucleotides having modifications in their internucleotide linkages have been shown to be more effective than their unmodified counterparts. For example, Agrawal et al. (*Proc. Natl. Acad. Sci.* (USA) (1988) 85:7079–7083) teaches that oligonucleotide phosphorothioates and certain oligonucleotide phosphoramidates are more effective at inhibiting HIV-1 than conventional phosphodiester-linked oligodeoxynucleotides. Agrawal et al. (*Proc. Natl. Acad. Sci.* (USA) (1989) 86:7790–7794) discloses the advantage of oligonucleotide phosphorothioates in inhibiting HIV-1 in early and chronically infected cells.

In addition, chimeric oligonucleotides having more than one type of internucleotide linkage within the oligonucleotide have been developed. Pederson et al. (U.S. Pat. Nos. 5,149,797 and 5,220,007 discloses chimeric oligonucleotides having an oligonucleotide phosphodiester or oligonucleotide phosphorothioate core sequence flanked by nucleotide methylphosphonates or phosphoramidates. Furdon et al. (*Nucleci Acids Res.* (1989) 17:9193–9204) discloses chimeric oligonucleotides having regions of oligonucleotide phosphodiesters in addition to either oligonucleotide phosphorothioate or methylphosphonate regions. Quartin et al. (*Nucleic Acids Res.* (1989) 17:7523–7562) discloses chimeric oligonucleotides having regions of oligonucleotide phosphodiesters and oligonucleotide methylphosphonates. Inoue et al. (*FEBS Lett.* (1987) 215:237–250) discloses chimeric oligonucleotides having regions of deoxyribonucleotides and 2'-O-methylribonucleotides.

Many of these modified oligonucleotides have contributed to improving the potential efficacy of the antisense oligonucleotide therapeutic approach. However, certain deficiencies remain in the known oligonucleotides, and these deficiencies can limit the effectiveness of such oligonucleotides as therapeutic agents. For example, Wickstrom (*J. Biochem Biophys. Meth.* (1986) 13:97–102) teaches that oligonucleotide phosphodiesters are susceptible to nuclease-mediated degradation, thereby limiting their bioavailability in vivo. Agrawal et al. (*Proc. Natl. Acad. Sci.* (USA) (1990) 87:1401–1405) teaches that oligonucleotide phosphoramidates or methylphosphonates when hybridized to RNA do not activate RNase H, the activation of which can be important to the function of antisense oligonucleotides. Thus, a need for methods of controlling gene expression exists which uses oligonucleotides with improved therapeutic characteristics.

Several reports have been published on the development of phosphorothioate-linked oligonucleotides as potential anti-AIDS therapeutic agents. Although extensive studies on chemical and molecular mechanisms of oligonucleotides have demonstrated the potential value of this novel therapeutic strategy, little is known about the pharmacokinetics and metabolism of these compounds in vivo.

Several preliminary studies on this topic have been published. Agrawal et al. (*Proc. Natl. Acad. Sci.*(USA) (1991) 88:7595–7599) describes the intravenous and intraperitoneal administration to mice of a 20mer phosphorothioate linked-oligonucleotide. In this study, approximately 30% of the administered dose was excreted in the urine over the first 24 hours with accumulation preferentially in the liver and kidney. Plasma half-lives ranged from about 1 hour ($t_{1/2\alpha}$) and 40 hours ($t_{1/2\beta}$), respectively. Similar results have been reported in subsequent studies (Iversen (1991) *Anti-Cancer Drug Design* 6:531–538; Iversen (1994) *Antisense Res. Devel.* 4:43–52; and Sands (1994) *Mol.Phann.* 45:932–943). However, stability problems may exist when oligonucleotides are administered intravenously and intraperitoneally. More recently, Agrawal et al. reported that oligonucleotide hybrids containing 2'-O-methyl ribonucleotides at both the 3'- and 5' ends and deoxyribonucleotide phosphorothioates in the interior portion were absorbed through the gastrointestinal (GI) tract of rats (*Biochem. Pharm.* (1995) 50:571–576).

Thus, there remains a need to develop more effective therapeutic methods of down-regulating the expression of genes which can be easily manipulated to fit the animal and condition to be treated, and the gene to be targeted. Preferably, these methods should be simple, painless, and precise in effecting the target gene.

SUMMARY OF THE INVENTION

The present invention provides a method of down-regulating the expression of a gene in an animal which involves the administration of an oligonucleotide complementary to the gene via an oral route, thereby bypassing the complications which may be experienced during intravenous and other modes of in vivo administration.

It has been discovered that hybrid oligonucleotides with other than phosphodiester bonds and having at least one 2'-substituted ribonucleotide and chimeric oligonucleotides with at least two different types of internucleotide linkages are relatively stable in vivo following oral administration to an animal, and that these molecules are successfully absorbed from the gastrointestinal tract and distributed to various body tissues. This discovery has been exploited to develop the present invention, which is a method of down-regulating the expression of a gene in an animal.

This method is also a means of examining the function of various genes in an animal, including those essential to animal development. Presently, gene function can only be examined by the arduous task of making a "knockout" animal such as a mouse. This task is difficult, time-consuming and cannot be accomplished for genes essential to animal development since the "knock out" would produce a lethal phenotype. The present invention overcomes the shortcomings of this model.

In the method of the invention, a pharmaceutical formulation containing an oligonucleotide complementary to the targeted gene is orally administered in a pharmaceutically acceptable carrier to the animal harboring the gene. The oligonucleotide inhibits the expression of the gene, thereby down-regulating its expression.

For purposes of the invention, the term "animal" is meant to encompass humans as well as other mammals, as well as reptiles amphibians, and insects. The term "oral administration" refers to the provision of the formulation via the mouth through ingestion, or via some other part of the gastrointestinal system including the esophagus.

As used herein, the term "oligonucleotide" is meant to include polymers of two or more nucleotides or nucleotide analogs connected together via 5' to 3' internucleotide linkages which may include any linkages that are known in the antisense art, including non-phosphodiester linkages. Such molecules have a 3' terminus and a 5' terminus.

The term "non-phosphodiester-linkages" as used herein refers to a synthetic covalent attachment between the 5' end of one nucleotide and the 3' end of another nucleotide in which the 5' nucleotide phosphate has been replaced with any number of chemical groups. Preferable synthetic linkages include alkylphosphonates, phosphorothioates, phosphorodithioates, alkylphosphonothioates, phosphoramidates, phosphoramidites, phosphate esters, carbamates, carbonates, phosphate triesters, acetamidate, and carboxymethyl esters. In one preferred embodiment of the invention, all of the nucleotides of the oligonucleotide are linked via phosphorothioate and/or phosphorodithioate linkages.

In some embodiments of the invention, the oligonucleotides administered are modified with other than, or in addition to, non-phosphodiester-internucleotide linkages. As used herein, the term "modified oligonucleotide" encompasses oligonucleotides with modified nucleic acid(s), base (s), and/or sugar(s) other than those found in nature. For example, a 3', 5'-substituted oligonucleotide is an oligonucleotide having a sugar which, at both its 3' and 5' positions is attached to a chemical group other than a hydroxyl group (at its 3' position) and other than a phosphate group (at its 5' position).

A modified oligonucleotide may also be one with added substituents such as diamines, cholestryl, or other lipophilic groups, or a capped species. In addition, unoxidized or partially oxidized oligonucleotides having a substitution in one nonbridging oxygen per nucleotide in the molecule are also considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention are also considered herein as modified.

In one embodiment, the oligonucleotide being administered in the method of the invention has non-phosphodiester internucleotide linkages and includes at least one 2'-substituted ribonucleotide.

For purposes of the invention, the term "2'-substituted oligonucleotide" refers to an oligonucleotide having a sugar attached to a chemical group other than a hydroxyl group at its 2' position. The 2'-OH of the ribose molecule can be substituted with -O-lower alkyl containing 1–6 carbon atoms, aryl or substituted aryl or allyl having 2–6 carbon atoms, e.g., 2'-O-allyl, 2'-O-aryl, 2'-O-alkyl (such as a 2'-O-methyl), 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups.

In one preferred embodiment of the invention, the oligonucleotide administered includes at least one 2'-substituted ribonucleotide at its 3' terminus. In some embodiments, all but four or five nucleotides at its 5' terminus are 2'-substituted ribonucleotides, and in some embodiments, these four or five unsubstituted 5' nucleotides are deoxyribonucleotides. In other embodiments, the oligonucleotide has at least one 2'-substituted ribonucleotide at both its 3' and 5' termini, and in yet other embodiments, the oligonucleotide is composed of 2'-substituted ribonucleotides in all positions with the exception of at least four or five contiguous deoxyribonucleotide nucleotides in any interior position. Another aspect of the invention includes the administration of an oligonucleotide composed of nucleotides that are all 2'-substituted ribonucleotides. Particular embodiments include oligonucleotides having a 2'-O-alkyl-ribonucleotide such as a 2'-O-methyl. Other embodiments include the administration of chimeric oligonucleotides. In one preferred embodiment, the chimeric oligonucleotide has at least one alkylphosphonate internucleotide linkage at both its 3' and 5' ends and having phosphorothioate internucleotide linkages.

In another embodiment of the invention, the oligonucleotide administered has at least one deoxyribonucleotide, and in a preferred embodiment, the oligonucleotide has at least four or five contiguous deoxyribonucleotides capable of activating RNase H.

The oligonucleotide administered is complementary to a gene of a virus, pathogenic organism, or a cellular gene in some embodiments of the invention. In some embodiments, the oligonucleotide is complementary to a gene of a virus involved in AIDS, oral or genital herpes, papilloma warts, influenza, foot and mouth disease, yellow fever, chicken pox, shingles, adult T-cell leukemia, Burkitt's lymphoma, nasopharyngeal carcinoma, or hepatitis. In one particular embodiment, the oligonucleotide is complementary to an HIV gene and includes about 15 to 26 nucleotides linked by phosphorothioate internucleotide linkages, at least one of the nucleotides at the 3' terminus being a 2'-substituted ribonucleotide, and at least four contiguous deoxyribonucleotides.

In another embodiment, the oligonucleotide is complementary to a gene encoding a protein associated with Alzheimer's disease.

In yet other embodiments, the oligonucleotide is complementary to a gene encoding a protein expressed in a parasite that causes a parasitic disease such as amebiasis, Chagas' disease, toxoplasmosis, pneumocytosis, giardiasis, cryptoporidiosis, trichomoniasis, malaria, ascariasis, filariasis, trichinosis, or schistosomiasis infections.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1:
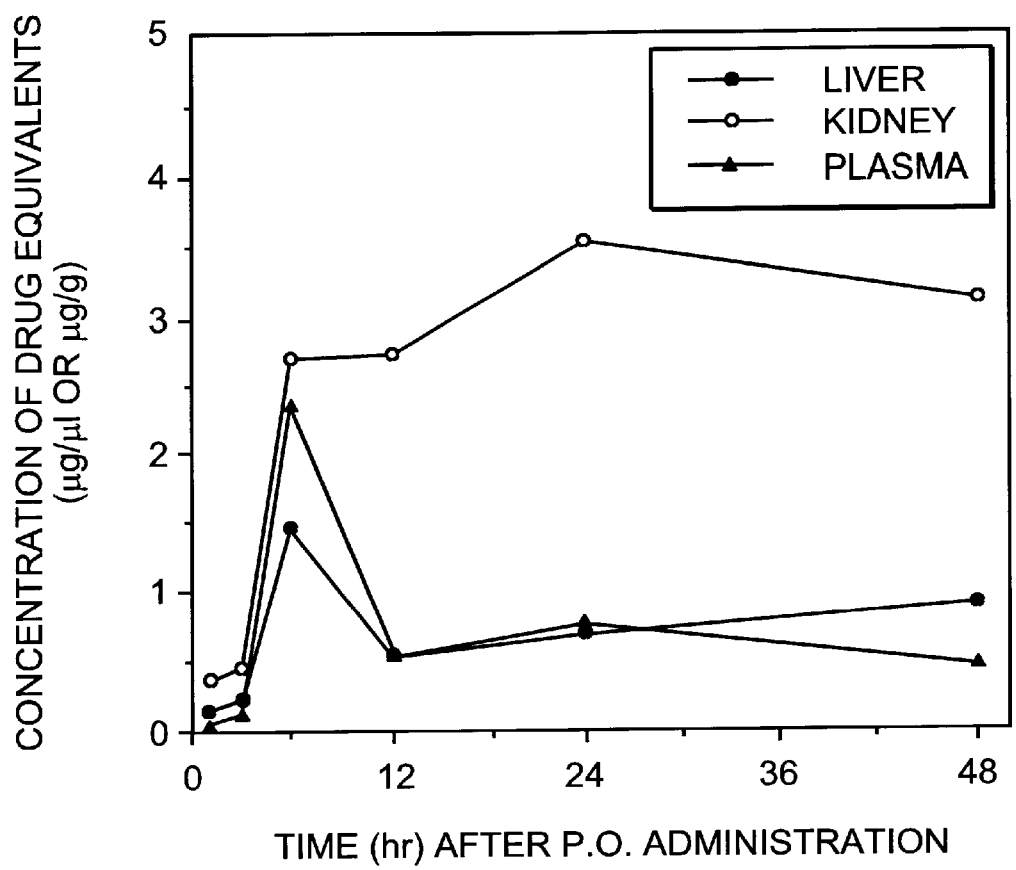
FIG. 1 is a graphic representation showing the time course of radiolabelled oligonucleotide in liver, kidney and plasma following the oral administration of radiolabelled phosphorothioate (PS) oligonucleotide 11 (SEQ ID NO:10)

The patent and scientific literature referred to herein establishes the knowledge that is available to those with skill in the art. The issued U.S. patent, allowed patent applications, and articles cited herein are hereby incorporated by reference.

This invention provides a method of down-regulating the expression of a gene in an animal by the oral administration of an oligonucleotide whose nucleotide sequence is complementary to the targeted gene.

It is known that an oligonucleotide, called an "antisense oligonucleotide," can bind to a target single-stranded nucleic acid molecule according to the Watson-Crick or the Hoogsteen rule of base pairing, and in doing so, disrupt the function of the target by one of several mechanisms: by preventing the binding of factors required for normal transcription, splicing, or translation; by triggering the enzymatic destruction of MRNA by RNase H if a contiguous region of deoxyribonucleotides exists in the oligonucleotide, and/or by destroying the target via reactive groups attached directly to the antisense oligonucleotide.

Thus, because of the properties described above, such oligonucleotides are useful therapeutically by their ability to control or down-regulate the expression of a particular gene in an animal, according to the method of the present invention.

The oligonucleotides useful in the method of the invention are at least 6 nucleotides in length, but are preferably 6 to 50, more preferably 11 to 35, most preferably 15 to 30, and commonly 15 to 25 nucleotides in length. They are composed of deoxyribonucleotides, ribonucleotides, or a combination of both, with the 5' end of one nucleotide and the 3' end of another nucleotide being covalently linked by non-phosphodiester internucleotide linkages. Such linkages include alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. Oligonucleotides with these linkages can be prepared according to known methods such as phosphoramidate or H-phosphonate chemistry which can be carried out manually or by an automated synthesizer as described by Brown (*A Brief History of Oligonucleotide Synthesis. Protocols for Oligonucleotides and Analogs, Methods in Molecular Biology* (1994) 20:1–8). (See also, e.g., Sonveaux "Protecting Groups in Oligonucleotides Synthesis" in Agrawal (1994) *Methods in Molecular Biology* 26:1–72; Uhlmann et al. (1990) Chem Rev. 90: 543–583).

The oligonucleotides of the composition may also be modified in a number of ways without compromising their ability to hybridize to the target nucleic acid. Such modifications include, for example, those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule. For the preparation of such modified oligonucleotides, see, e.g., Agrawal (1994) *Methods in Molecular Biology* 26; Uhlmann et al. (1990) *Chem Rev.* 90:543–583).

Oligonucleotides which are self-stabilized are also considered to be modified oligonucleotides useful in the methods of the invention (Tang et al. (1993) *Nucleic Acids Res.* 20:2729–2735). These oligonucleotides comprise two regions: a target hybridizing region; and a self-complementary region having an oligonucleotide sequence complementary to a nucleic acid sequence that is within the self-stabilized oligonucleotide.

The preparation of these unmodified and modified oligonucleotides is well known in the art (reviewed in Agrawal et al. (1992) *Trends Biotechnol.* 10:152–158) (see, e.g., Uhlmann et al. (1990) *Chem Rev.* 90:543–584; and (1987) *Tetrahedron. Lett.* 28:(31):3539–3542); Agrawal (1994) *Methods in Molecular Biology* 20:63–80); and Zhang et al. (1996) *J. Pharmacol. Expt. Thera.* 278:1–5).

The oligonucleotides administered to the animal may be hybrid oligonucleotides in that they contain both deoxyribonucleotides and at least one 2' substituted ribonucleotide. For purposes of the invention, the term "2'-substituted" means substitution at the 2' position of the ribose with, e.g., a -O-lower alkyl containing 1–6 carbon atoms, aryl or substituted aryl or allyl having 2–6 carbon atoms e.g., 2'-O-allyl, 2'-O-aryl, 2'-O-alkyl, 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups. Useful substituted ribonucleotides are 2'-O-alkyls such as 2'-O-methyl.

The hybrid DNA/RNA oligonucleotides useful in the method of the invention resist nucleolytic degradation, form stable duplexes with RNA or DNA, and preferably activate RNase H when hybridized with RNA. They may additionally include at least one unsubstituted ribonucleotide. For example, an oligonucleotide useful in the method of the invention may contain all deoxyribonucleotides with the exception of one 2' substituted ribonucleotide at the 3' terminus of the oligonucleotide. Alternatively, the oligonucleotide may have at least one substituted ribonucleotide at both its 3' and 5' termini.

One preferred class of oligonucleotides useful in the method of the invention contains four or more deoxyribonucleotides in a contiguous block, so as to provide an activating segment for RNase H. In certain cases, more than one such activating segment will be present at any location within the oligonucleotide. There may be a majority of deoxyribonucleotides in oligonucleotides according to the invention. In fact, such oligonucleotides may have as many as all but one nucleotide being deoxyribonucleotides. Thus, a preferred oligonucleotide having from about 2 to about 50 nucleotides or most preferably from about 12 to about 25 nucleotides, the number of deoxyribonucleotides present ranges from 1 to about 24. Other useful oligonucleotides may consist only of 2'-substituted ribonucleotides.

TABLE 1 lists some representative species of oligonucleotides which are useful in the method of the invention. 2'-substituted nucleotides are underscored.

TABLE 1

| OLIGO NO. | OLIGONUCLEOTIDE | SEQ ID NO.: |
|---|---|---|
| 1 | CTCTCGCACCCATCTCTCTCCTTC_U_ | 1 |
| 2 | CTCTCGCACCCATCTCTCTCCT_UCU_ | 2 |
| 3 | CTCTCGCACCCATCTCTCT_CCUUCU_ | 3 |
| 4 | CTCTCGCACCCATCT_CUCUCCUUCU_ | 4 |
| 5 | CTCTCGCACCC_AUCUCUCUCCUUCU_ | 5 |
| 6 | CTCT_CGCACCCAUCUCUCUCCUUCU_ | 6 |
| 7 | CTCT_CGCACCCAUCUCUCUCCUUCU_ | 7 |
| 8 | _CUCUCGCACCCAUCUCUCUCCUUCU_ | 8 |
| 9 | _CTCTCGCACCCATCTCTCTCCTTCU_ | 1 |
| 10 | _CUCTCGCACCCATCTCTCTCCTTCU_ | 9 |
| 11 | _CUCUCGCACCCATCTCTCTCCUUCU_ | 10 |
| 12 | _CUCUCGCACCCATCTCUCUCCUUCU_ | 11 |
| 13 | _CUCUCGCACCCAUCUCUCUCCUUCU_ | 12 |
| 14 | _CUCUCGCACCCATCTCTCUCCUUCU_ | 13 |
| 15 | _CTCTCGCACCCAUCUCUCUCCUUCU_ | 5 |
| 16 | _CUCUCGCACCCAUCTCTCTCCUUCU_ | 14 |
| 17 | _CUCUCGCACCCATCTCTCTCCUUCU_ | 15 |
| 18 | _CUCTCGCACCCAUCUCUCUCCUUCU_ | 16 |
| 19 | _CUCTCGCACCCATCTCTCUCCUUCU_ | 17 |

The oligonucleotides administered to the animal may be chimeric in that they contain more than one type of internucleotide linkage. Such chimeric oligonucleotides are described in U.S. Pat. Nos. 5,149,797 and 5,366,878. For example, chimeric oligonucleotides useful in the method of the invention may include phosphorothioate and alkylphosphonate internucleotide linkages. One preferred alkylphosphonate linkage is a methylphosphonate linkage.

Table 2 lists some representative specifics of chimeric oligonucleotides which are useful in the method of the invention. The alkylphosphonate internucleotide linkages are indicated by ":"; the phosphorothioate linkages are indicated by "-".

TABLE 2

| NO: | OLIGONUCLEOTIDE (5'→3') | SEQ ID NO: |
|---|---|---|
| 20 | C:T:C:T-C-G-C-A-C-C-A-T-C-T-C-T-C-T-C-C:T:T:C:T | 18 |
| 21 | C:T:C:T-C-G-C-A-C-C-A-T-C-T-C-T-C-T-C-C-T:T:C:T | 18 |
| 22 | C:T:C:T:C-G-C-A-C-C-A-T-C-T-C-T-C-T-C-C:T:T:C:T | 18 |
| 23 | C:T:C-T-C-G-C-A-C-C-A-T-C-T-C-T-C-T-C-C:T:T:C:T | 18 |
| 24 | C:T:C-T-C-G-C-A-C-C-A-T-C-T-C-T-C-T-C-C-T:T:C:T | 18 |
| 25 | C:T:C:T-C-G-C-A-C-C-A-T-C-T-C-T-C-T-C-C-T-T:C:T | 18 |
| 26 | C:T:C:T:C-G-C-A-C-C-A-T-C-T-C-T-C-T-C-C-T-T:C:T | 18 |
| 27 | C:T:C-T-C-G-C-A-C-C-A-T-C-T-C-T-C-T-C-C-T-T:C:T | 18 |
| 28 | C:T:C:T:C-G-C-A-C-C-A-T-C-T-C-T-C-T-C-C-T:T:C:T | 18 |
| 29 | C:T-C-T-C-G-C-A-C-C-A-T-C-T-C-T-C-T-C-C:T:T:C:T | 18 |
| 30 | C:T-C-T-C-G-C-A-C-C-A-T-C-T-C-T-C-T-C-C-T:T:C:T | 18 |
| 31 | C:T:C:T-C-G-C-A-C-C-A-T-C-T-C-T-C-T-C-C-T-T-C:T | 18 |
| 32 | C:T:C:T-C-G-C-A-C-C-A-T-C-T-C-T-C-T-C-C-T-T-C:T | 18 |
| 33 | C:T:C:T-C-G-C-A-C-C-A-T-C-T-C-T-C-T-C-C:T | 19 |
| 34 | C:T:C:T-C-G-C-A-C-C-A-T-C-T-C-T-C-T-C-C-T | 19 |
| 35 | C:T:C:T:C-G-C-A-C-C-A-T-C-T-C-T-C-T-C-C:T | 19 |
| 36 | C:T:C-T-C-G-C-A-C-C-A-T-C-T-C-T-C-T-C-C:T | 19 |
| 37 | C:T:C-T-C-G-C-A-C-C-A-T-C-T-C-T-C-T-C-C-T | 19 |
| 38 | C:T:C:T-C-G-C-A-C-C-A-T-C-T-C-T-C-T-C-C-T | 19 |
| 39 | C:T:C:T:C-G-C-A-C-C-A-T-C-T-C-T-C-T-C-C-T | 19 |
| 40 | C:T:C-T-C-G-C-A-C-C-A-T-C-T-C-T-C-T-C-C-T | 19 |
| 41 | C:T:C:T:C-G-C-A-C-C-A-T-C-T-C-T-C-T-C-C-T | 19 |
| 42 | C:T-C-T-C-G-C-A-C-C-A-T-C-T-C-T-C-T-C-C:T | 19 |
| 43 | C:T-C-T-C-G-C-A-C-C-A-T-C-T-C-T-C-T-C-C-T | 19 |
| 44 | C:T:C:T-C-G-C-A-C-C-A-T-C-T-C-T-C-T-C-C-T | 19 |
| 45 | C:T:C:T-C-G-C-A-C-C-A-T-C-T-C-T-C-T-C-C-T | 19 |

The oligonucleotides according to the invention are effective in inhibiting the expression of various genes in viruses, pathogenic organisms, or in inhibiting the expression of cellular genes. The ability to inhibit such agents is clearly important to the treatment of a variety of disease states. Thus, oligonucleotides according to the method of the invention have a nucleotide sequence which is complementary to a nucleic acid sequence that is from a virus, a pathogenic organism or a cellular gene. Preferably such oligonucleotides are from about 6 to about 50 nucleotides in length.

For purposes of the invention, the term "oligonucleotide sequence that is complementary to a nucleic acid sequence", is intended to mean an oligonucleotide sequence that binds to the target nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, pseudoknot formation. Such binding (by Watson Crick base pairing) under physiological conditions is measured as a practical matter by observing interference with the function of the nucleic acid sequence.

The nucleic acid sequence to which an oligonucleotide according to the invention is complementary will vary, depending upon the gene to be down-regulated. In some cases, the target gene or nucleic acid sequence will be a virus nucleic acid sequence. The use of antisense oligonucleotides to inhibit various viruses is well known (reviewed in Agrawal (1992) Trends in Biotech. 10:152–158). Viral nucleic acid sequences that are complementary to effective antisense oligonucleotides have been described for many viruses, including human immunodeficiency virus type 1 (HIV-1) (U.S. Pat. No. 4,806,463), herpes simplex virus (U.S. Pat. No. 4,689,320), influenza virus (U.S. Pat. No. 5,194,428), and human papilloma virus (Storey et al. (1991) Nucleic Acids Res. 19:4109–4114 ). Sequences complementary to any of these nucleic acid sequences can be used for oligonucleotides according to the invention, as can be oligonucleotide sequences complementary to nucleic acid sequences from any other virus. Additional viruses that have known nucleic acid sequences against which antisense oligonucleotides can be prepared include, but are not limited to, foot and mouth disease virus (see, Robertson et al. (1985) J. Virol. 54:651; Harris et al. (1980) Virol. 36:659), yellow fever virus (see Rice et al. (1985) Science 229;726), varicella-zoster virus (see, Davison and Scott (1986) J. Gen. Virol. 67:2279), Epstein-Barr virus, cytomegalovirus, respiratory syncytial virus (RSV), and cucumber mosaic virus (see Richards et al. (1978) Virol. 89:395).

For example, an oligonucleotide has been designed which is complementary to a portion of the HIV-1 gene, and as such, has significant anti-HIV effects (Agrawal (1992) Antisense Res. Development 2:261–266). The target of this oligonucleotide has been found to be conserved among various HIV-1 isolates. It is 56% G+C rich, water soluble, and relatively stable under physiological conditions. This oligonucleotide binds to a complementary RNA target under physiological conditions, with the T of the duplex approximately being 56° C. The antiviral activity of this oligonucleotide has been tested in several models, including acutely and chronically infected CEM cells, long-term cultures mimicking in vivo conditions, human peripheral blood lymphocytes and macrophages, and isolates from HIV-1 infected patients (Lisziewicz et al. (Proc. Natl. Acad. Sci. (USA) (1992) 89:11209–11213); Lisziewicz et al. (Proc. Natl. Acad. Sci. (USA) (1993) 90:3860–3864); Lisziewicz et al. (Proc. Natl. Acad. Sci. (USA) (1994) 91:7942–7946); Agrawal et al. (J. Ther. Biotech) in press).

The oligonucleotides according to the invention alternatively can have an oligonucleotide sequence complementary to a nucleic acid sequence of a pathogenic organism. The nucleic acid sequences of many pathogenic organisms have been described, including the malaria organism, Plasmodium falciparum, and many pathogenic bacteria. Oligonucleotide sequences complementary to nucleic acid sequences from any such pathogenic organism can be used in oligonucleotides according to the invention. Nonlimiting examples of pathogenic eucaryotes having known nucleic acid sequences against which antisense oligonucleotides can be prepared include *Trypanosom abrucei gambiense* and *Leishmania* (See Campbell et al., *Nature* 311:350 (1984)), and *Fasciola hepatica* (See Zurita et al., *Proc. Natl. Acad. Sc. USA* 84:2340 (1987).

Antifungal oligonucleotides can be prepared using a target hybridizing region having an oligonucleotide sequence that is complementary to a nucleic acid sequence from, e.g., the chitin synthetase gene, and antibacterial oligonucleotides can be prepared using, e.g., the alanine racemase gene. Among fungal diseases that may be treatable by the method of treatment according to the invention are candidiasis, histoplasmosis, cryptococcocis, blastomycosis, aspergillosis, sporotrichosis, chromomycosis, dermatophytosis, and coccidioidomycosis. The method might also be used to treat rickettsial diseases (e.g., typhus, Rocky Mountain spotted fever), as well as sexually transmitted diseases caused by Chlamydia trachomatis or Lymphogranuloma venereum. A variety of parasitic diseases may be treated by the method according to the invention, including amebiasis, Chagas' disease, toxoplasmosis, pneumocystosis, giardiasis, cryptosporidiosis, trichomoniasis, and Pneumocystis carini pneumonia; also worm (helminthic) diseases such as ascariasis, filariasis, trichinosis, schistosomiasis and nematode or cestode infections. Malaria may be treated by the method of treatment of the invention regardless of whether it is caused by P. falciparum, P. vivas, P. orale, or P. malariae.

The infectious diseases identified above may all be treated by the method of treatment according to the invention because the infectious agents for these diseases are known and thus oligonucleotides according to the invention can be prepared, having oligonucleotide sequence that is complementary to a nucleic acid sequence that is an essential nucleic acid sequence for the propagation of the infectious agent, such as an essential gene.

Other disease states or conditions that may be treatable by the method according to the invention are those which result from an abnormal expression or product of a cellular gene. These conditions may be treated by administration of oligonucleotides according to the invention, and have been discussed earlier in this disclosure.

Other oligonucleotides according to the invention can have a nucleotide sequence complementary to a cellular gene or gene transcript, the abnormal expression or product of which results in a disease state. The nucleic acid sequences of several such cellular genes have been described, including prion protein (Stahl et al. (1991) *FASEB J.* 5:2799–2807), the amyloid-like protein associated with Alzheimer's disease (U.S. Pat. No. 5,015,570), and various well-known oncogenes and proto-oncogenes, such as c-myb, c-myc, c-abl, and n-ras. In addition, oligonucleotides that inhibit the synthesis of structural proteins or enzymes involved largely or exclusively in spermatogenesis, sperm motility, the binding of the sperm to the egg or any other step affecting sperm viability may be used as contraceptives. Similarly, contraceptives for women may be oligonucleotides that inhibit proteins or enzymes involved in ovulation, fertilization, implantation or in the biosynthesis of hormones involved in those processes.

Hypertension may be controlled by oligonucleotides that down-regulate the synthesis of angiotensin converting enzyme or related enzymes in the renin/angiotensin system. Platelet aggregation may be controlled by suppression of the synthesis of enzymes necessary for the synthesis of thromboxane A2 for use in myocardial and cerebral circulatory disorders, infarcts, arteriosclerosis, embolism and thrombosis. Deposition of cholesterol in arterial wall may be inhibited by suppression of the synthesis of fatty acid co-enzyme A: cholesterol acyl transferase in arteriosclerosis. Inhibition of the synthesis of cholinephosphotransferase may be useful in hypolipidemia.

There are numerous neural disorders in which hybridization arrest may be used to reduce or eliminate adverse effects of the disorder. For example, suppression of the synthesis of monoamine oxidase may be used in Parkinson's disease. Suppression of catechol o-methyl transferase may be used to treat depression; and suppression of indole N-methyl transferase may be used in treating schizophrenia.

Suppression of selected enzymes in the arachidonic acid cascade which leads to prostaglandins and leukotrienes may be useful in the control of platelet aggregation, allergy, inflammation, pain and asthma.

Suppression of the protein expressed by the multidrug resistance (mdr-1) gene, which can be responsible for development of resistance of tumors to a variety of anti-cancer drugs and is a major impediment in chemotherapy may prove to be beneficial in the treatment of cancer. Oligonucleotide sequences complementary to nucleic acid sequences from any of these genes can be used for oligonucleotides according to the invention, as can be oligonucleotide sequences complementary to any other cellular gene transcript, the abnormal expression or product of which results in a disease state.

The oligonucleotides described herein are administered orally or enterally to the animal subject in the form of therapeutic pharmaceutical formulations that are effective for treating virus infection, infections by pathogenic organisms, or disease resulting from abnormal gene expression or from the expression of an abnormal gene product. In some aspects or the method according to the invention, the oligonucleotides are administered in conjunction with other therapeutic agents, e.g., AZT in the case of AIDS.

The therapeutic pharmaceutical formulation containing the oligonucleotide includes a physiologically acceptable carrier, such as an inert diluent or an assimilable edible carrier with which the peptide is administered. Suitable formulations that include pharmaceutically acceptable excipients for introducing compounds to the bloodstream by other than injection routes can be found in *Remington's Pharmaceutica Sciences* (18th ed.) (Genarro, ed. (1990) Mack Publishing Co., Easton, Pa.). The oligonucleotide and other ingredients may be enclosed in a hard or soft shell gelatin capsule, compressed into tablets, or incorporated directly into the individual's diet. The oligonucleotide may be incorporated with excipients and used in the form of ingestible tablets, buccal tablets, troches, capsules, elixirs, suspensions, syrups, wafers, and the like. When the oligonucleotide is administered orally, it may be mixed with other food forms and pharmaceutically acceptable flavor enhancers. When the oligonucleotide is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are also contemplated such as those described in U.S. Pat. Nos. 4,704,295, 4,556, 552, 4,309,404, and 4,309,406.

The amount of oligonucleotide in such therapeutically useful compositions is such that a suitable dosage will be obtained. Preferred compositions or preparations according to the present invention are prepared so that an oral dosage unit contains between from about 50 micrograms to about 200 mg per kg body weight of the animal, with 10 mg to 100 mg per kg being most preferable.

It will be appreciated that the unit content of active ingredient or ingredients contained in an individual dose of each dosage form need not in itself constitute an effective amount since the necessary effective amount can be reached by administration of a plurality of dosage units (such as capsules or tablets or combinations thereof).

In order to determine if the oligonucleotide administered according to the method of the invention is absorbed into body tissues, and if so, in which tissues absorption occurs, the following study was performed. Samples of various body tissues from treated rats were analyzed for radioactivity at increasing hours after oral administration of a radioactively labelled phosphorothioate oligonucleotide. FIG. 1 illustrates the plasma, liver, and kidney concentration-time course of an oligonucleotide equivalents after oral administration of the radiolabelled oligonucleotide. These results demonstrate that the drug is absorbed through gastrointestinal tract and accumulated in the kidney and the liver.

Figure 2A:
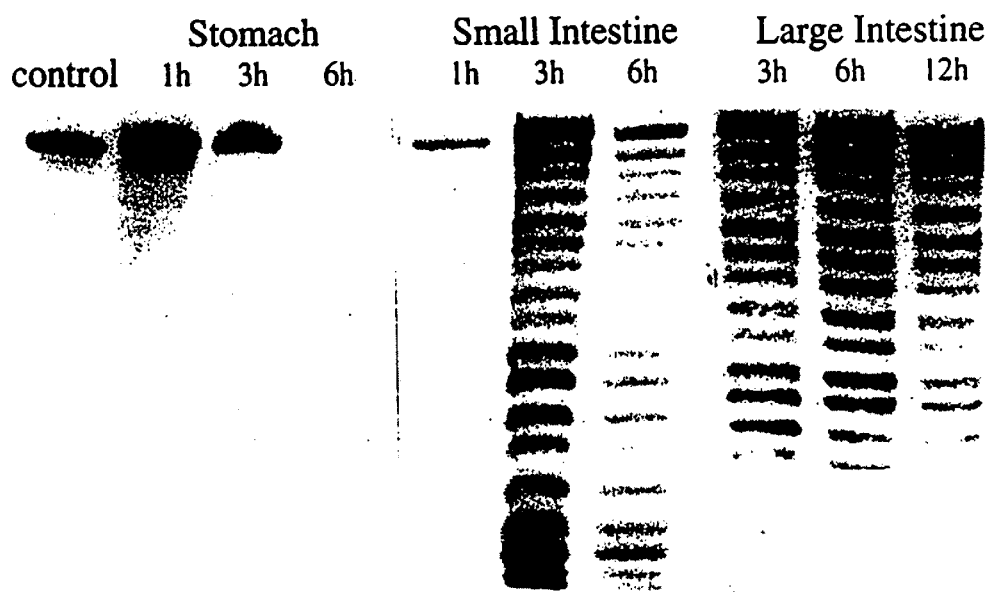
FIG. 2A is a representation of an autoradiogram of radiolabelled oligonucleotide in the stomach, small intestine, and large intestine of rats at different times following oral administration of PS oligonucleotide.
Figure 2B:
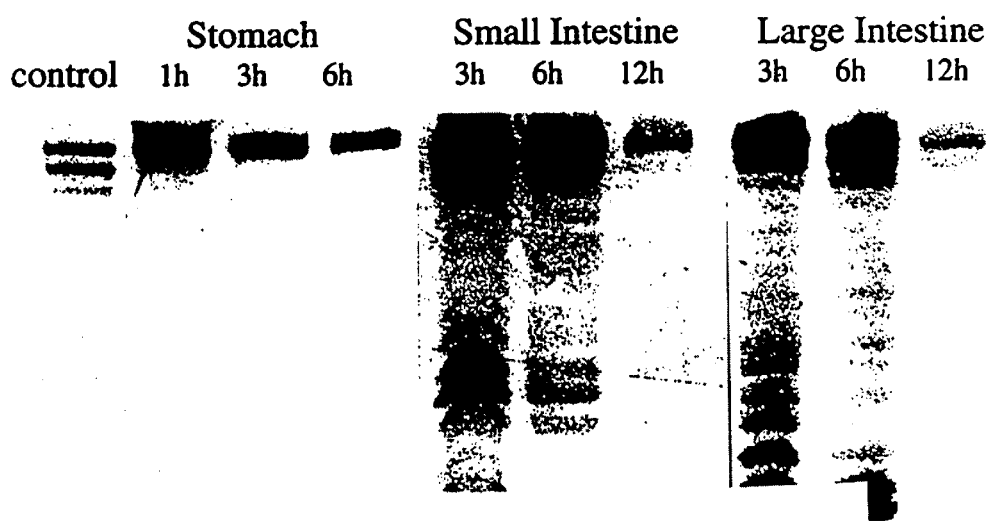
FIG. 2B is a representation of an autoradiogram of radiolabelled oligonucleotide in the stomach, small intestine, and large intestine of rats at different times following oral administration of hybrid oligonucleotide.

As illustrated in FIGS. 2A and 2B, both unmodified and hybrid oligonucleotides were shown to be stable in the stomach up to 6 hr following oral administration. The unmodified oligonucleotide underwent extensive degradation in small and large intestine, the majority of the radioactivity being associated with the different length of truncated oligonucleotide (FIG. 2A). In contrast, the hybrid oligonucleotide was more stable compared to the unmodified oligonucleotide, the majority of the radioactivity in small intestine being associated with the intact oligonucleotide (FIG. 2B). Increased degradation of the hybrid oligonucleotide was observed in the large intestine (FIG. 2B).

Figure 3A:
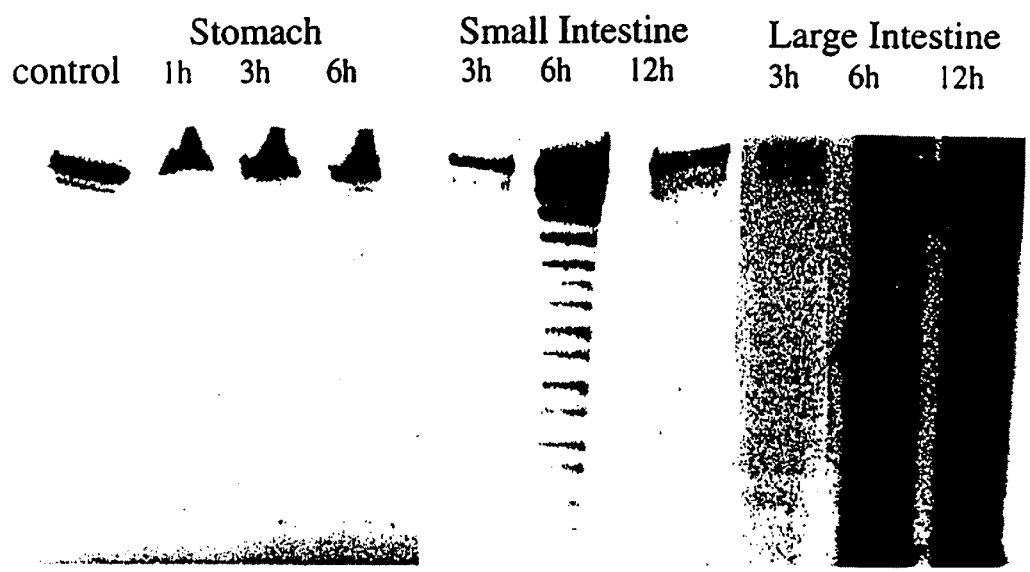
FIG. 3A is a representation of an autoradiogram of radiolabelled oligonucleotide in the stomach, small intestine, and large intestine of mice at different times following oral administration of hybrid oligonucleotide.
Figure 3B:
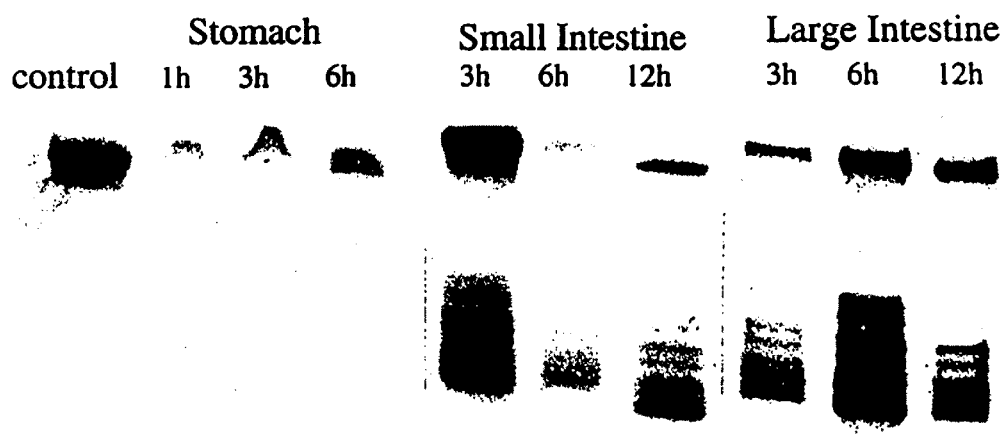
FIG. 3B is a representation of an autoradiogram of radiolabelled oligonucleotide in the stomach, small intestine, and large intestine of mice at different times following oral administration of chimeric oligonucleotide.

$^{35}$S-labelled modified oligonucleotides were also orally administered to mice at a single dose. For the hybrid oligonucleotide, similar profiles of gel electrophoresis of radioactivity in the gastrointestinal tract were observed with mice compared to rats (FIG. 3A). For the chimeric oligonucleotide, gel electrophoresis of radioactivity in the gastrointestinal tract revealed that this compound was stable in stomach and small intestine, with significant degradation in large intestine (FIG. 3B).

Figure 4A:
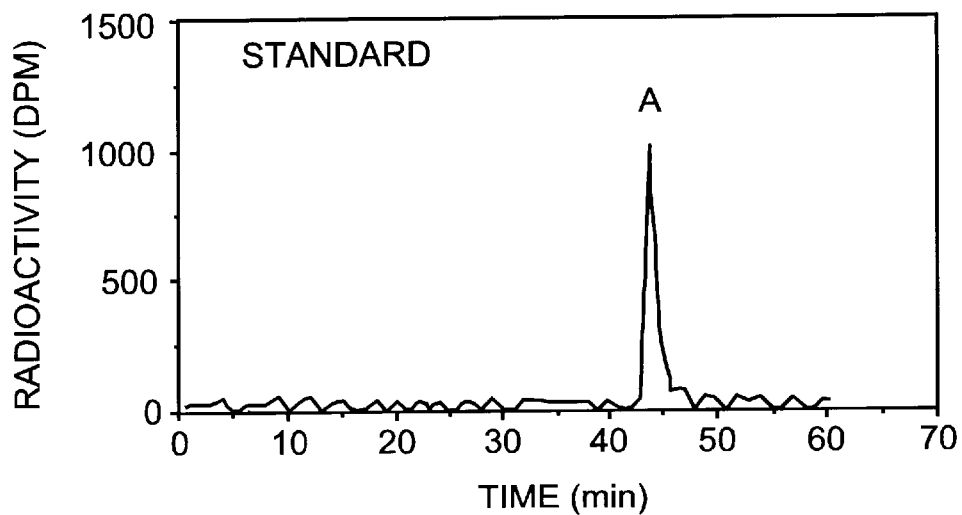
FIG. 4A is an HPLC chromatograph of radiolabelled PS oligonucleotide standard.
Figure 4B:
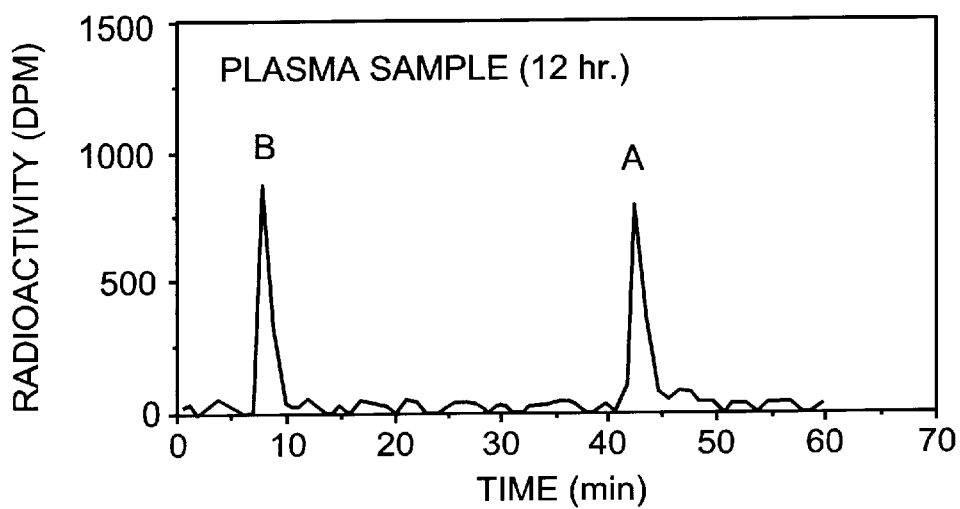
FIG. 4B is an HPLC chromatogram of oligonucleotides extracted from plasma samples taken 12 hours after the administration of radiolabelled PS oligonucleotide.
Figure 5A:
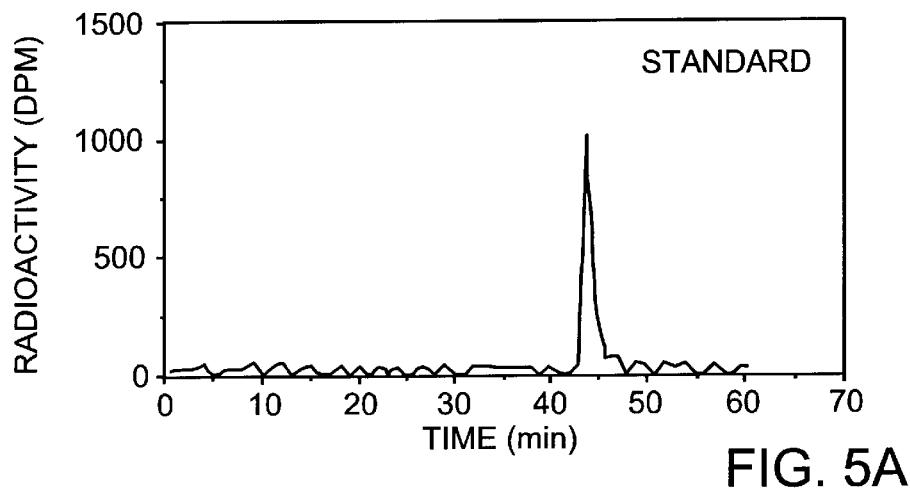
FIG. 5A is an HPLC chromatogram of radiolabelled PS oligonucleotide standard.
Figure 5B:
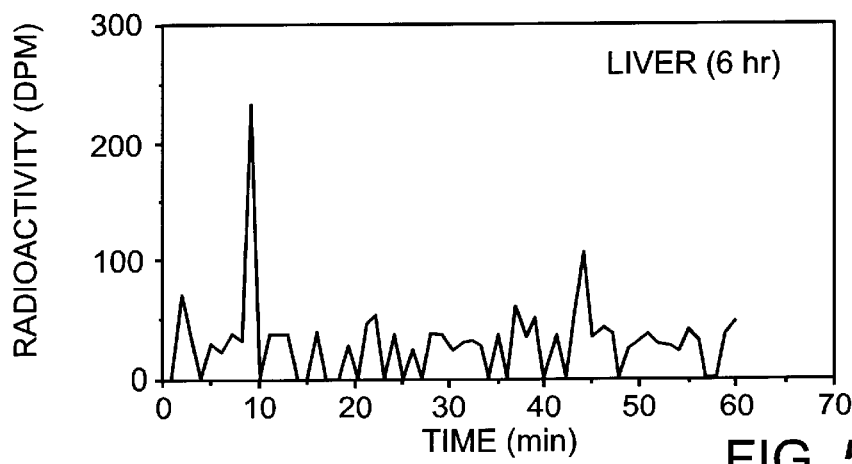
FIG. 5B is an HPLC chromatogram of oligonucleotides extracted from rat liver 6 hours after the administration of radiolabelled PS oligonucleotide.
Figure 5C:
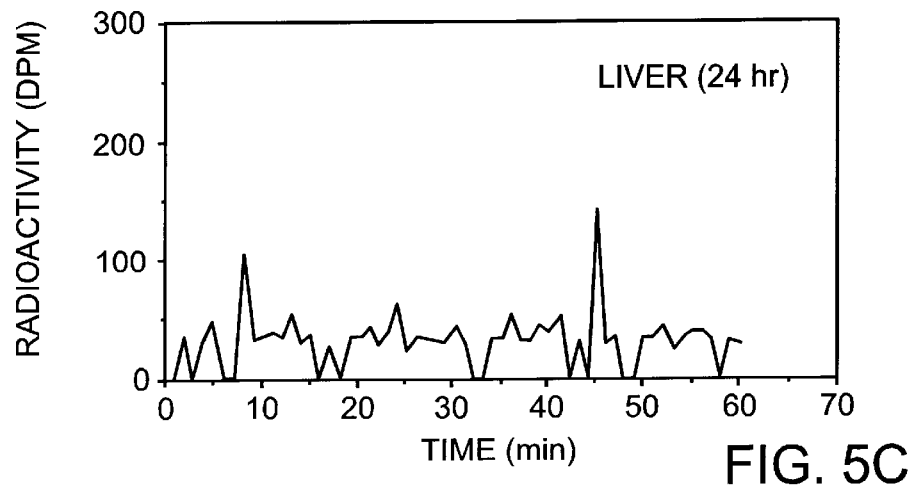
FIG. 5C is an HPLC chromatogram of oligonucleotides extracted from rat liver 24 hours after the administration of radiolabelled PS oligonucleotide.
Figure 11A:
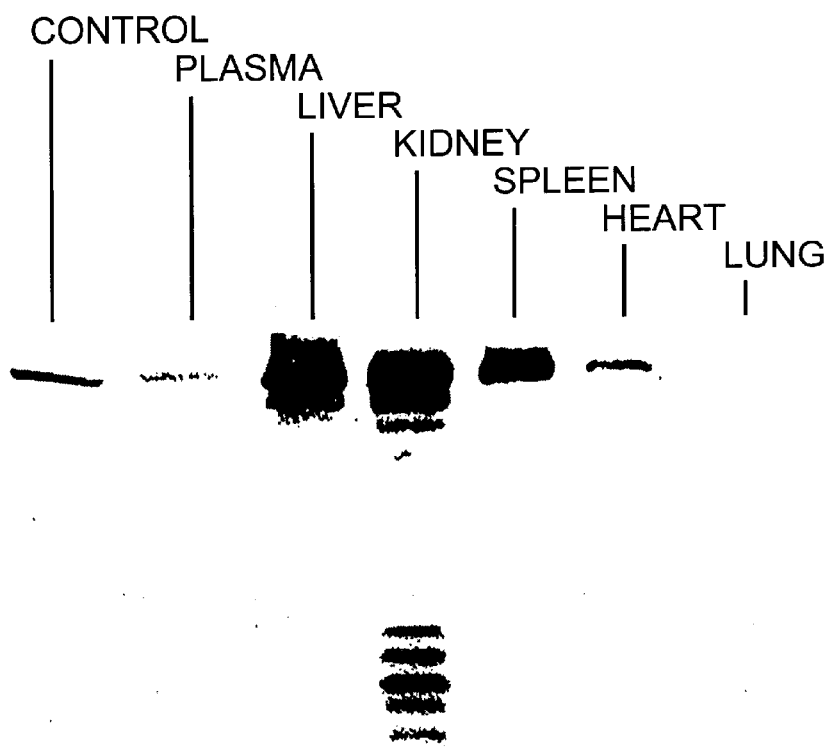
FIG. 11A is a representation of an autoradiogram of radiolabelled oligonucleotide in the plasma, liver, kidney, spleen, heart, and lung of mice 6 hours following oral administration of hybrid oligonucleotide.
Figure 11B:
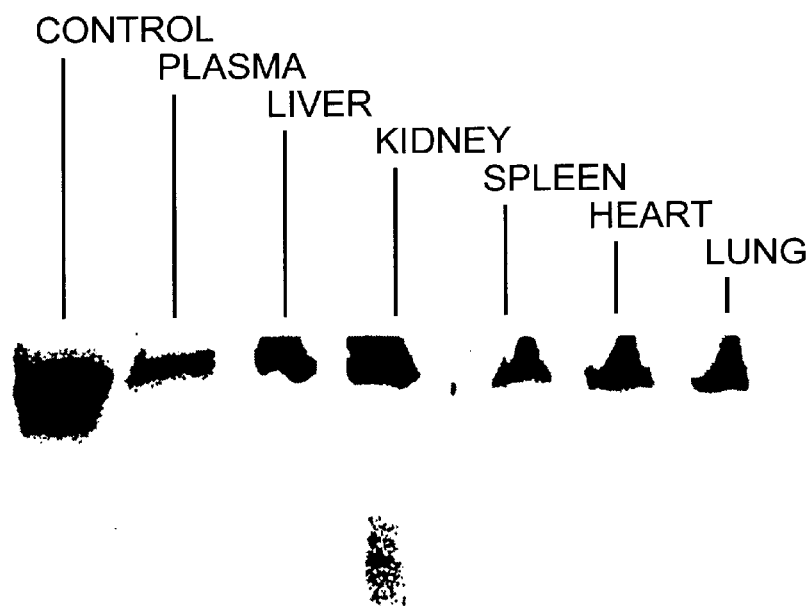
FIG. 11B is a representation of an autoradiogram of radiolabelled oligonucleotide in the plasma, liver, kidney, spleen, heart, and lung of mice 6 hours following oral administration of chimeric oligonucleotide.

The chemical form of radioactivity in rat plasma was further evaluated by HPLC as shown in FIGS. 4A and 4B, demonstrating the presence of both intact PS oligonucleotide (A) as well as metabolites (B) 12 hours after oral administration (see FIG. 4B). Intact oligonucleotide was also detected in rat liver 6 hours (FIG. 5B) and 12 hours (FIG. 5C) after oral administration. Radioactivity in rat brain, thymus, heart, lung, liver, kidney, adrenals, stomach, small intestine, large intestine, skeletal muscle, testes, thyroid, epidermis, whole eye, and bone marrow was detectable 48 hours after oral administration of the radiolabelled oligonucleotide. For unmodified oligonucleotide, minimal intact form was detectable in rat tissue samples. However, as shown in FIG. 11A for the hybrid oligonucleotide and in FIG. 11B for the chimeric oligonucleotide, intact oligonucleotides were detected in plasma and tissue samples of the liver, kidney, spleen, heart, and lung.

Figure 6:
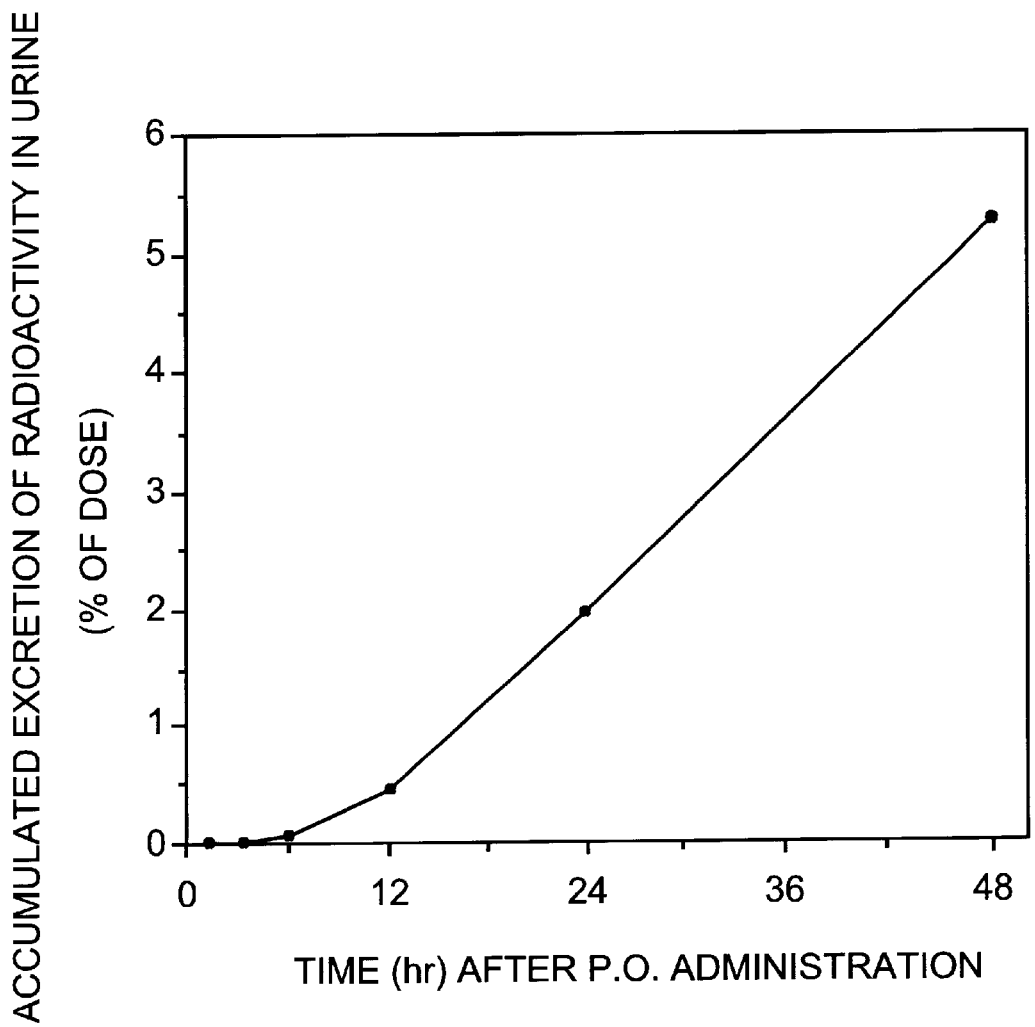
FIG. 6 is a graphic representation demonstrating the time course of urinary excretion of radioactivity in rats following the oral administration of radiolabelled PS oligonucleotide.
Figure 7A:
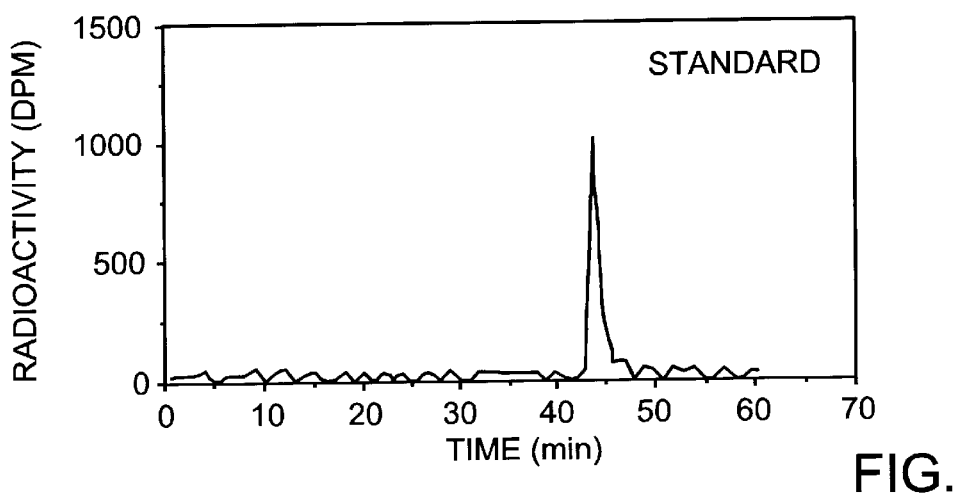
FIG. 7A is an HPLC chromatogram of radiolabelled PS oligonucleotide standard.
Figure 7B:
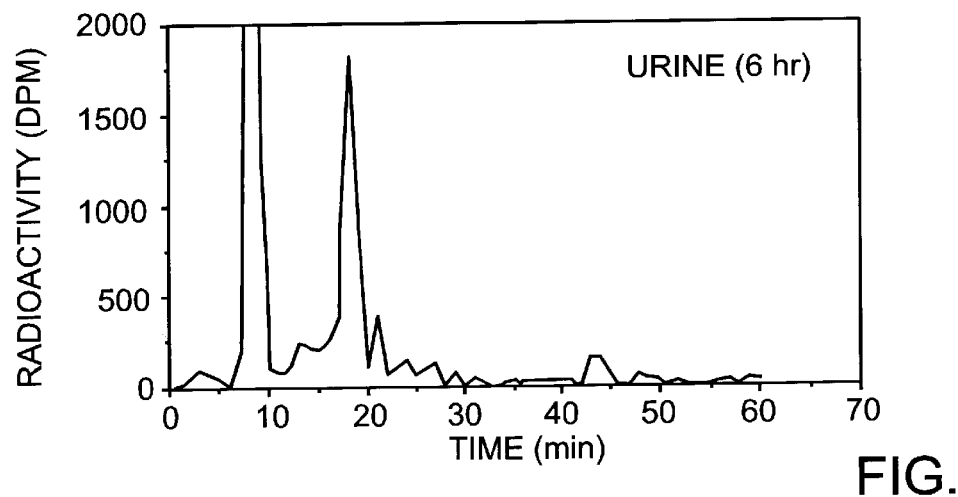
FIG. 7B is an HPLC chromatogram of oligonucleotides extracted from rat urine 6 hours after the administration of radiolabelled PS oligonucleotide.
Figure 7C:
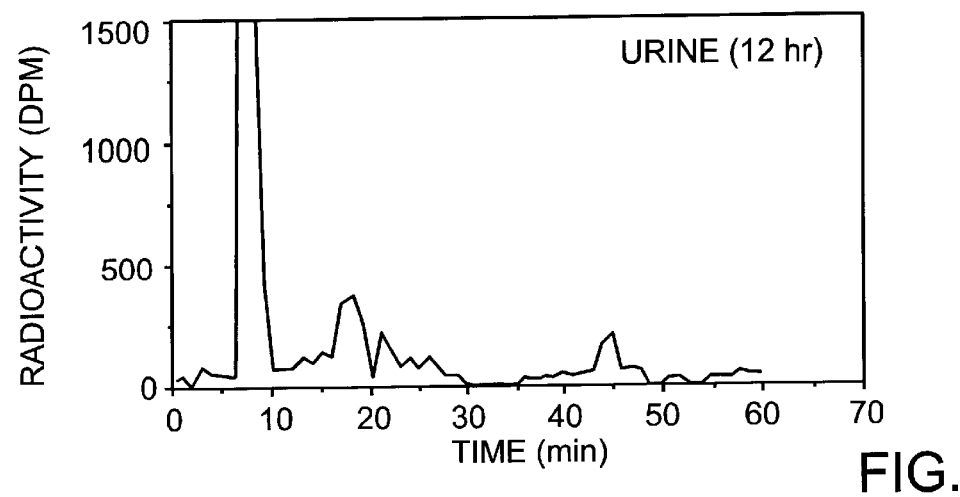
FIG. 7C is an HPLC chromatogram of oligonucleotides extracted from rat urine 12 hours after the administration of radiolabelled PS oligonucleotide.

Further evidence to support the absorption of the oligonucleotide comes from urine sample analysis after radioactively labelled oligonucleotide was orally administered. FIG. 6 shows the cumulative excretion of the radioactively labelled oligonucleotide into the urine over 48 hr following the administration of radiolabelled phosphorothioate oligonucleotide. That the oligonucleotide continues to be excreted in the urine over time implies that other tissues had absorbed it, and that the body was capable of absorption for an extended period of time. FIGS. 7B and 7C demonstrate that although the majority of radioactivity in urine was present as degradative products, intact oligonucleotide was also detected, demonstrating that this oligonucleotide is absorbed intact.

Figure 8:
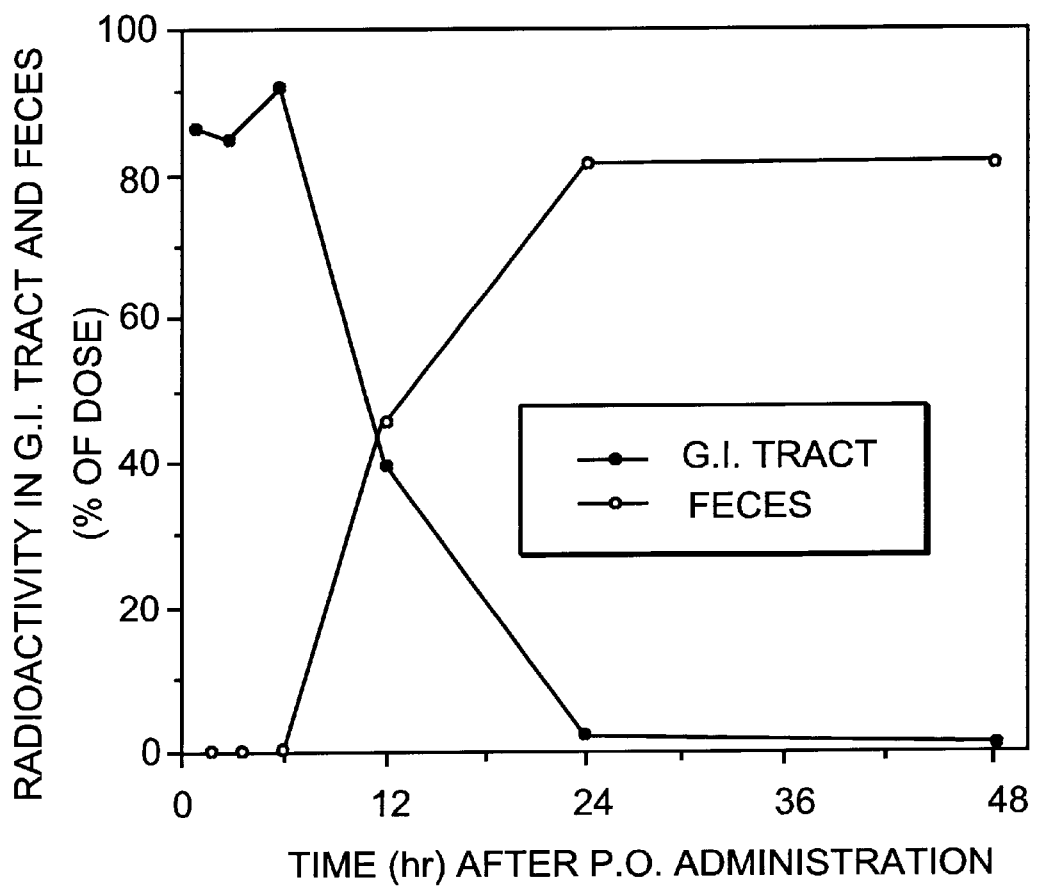
FIG. 8 is a graphic representation showing the course of radioactivity in the gastrointestinal tract and feces in rats following the oral administration of radiolabelled PS oligonucleotide.
Figure 9:
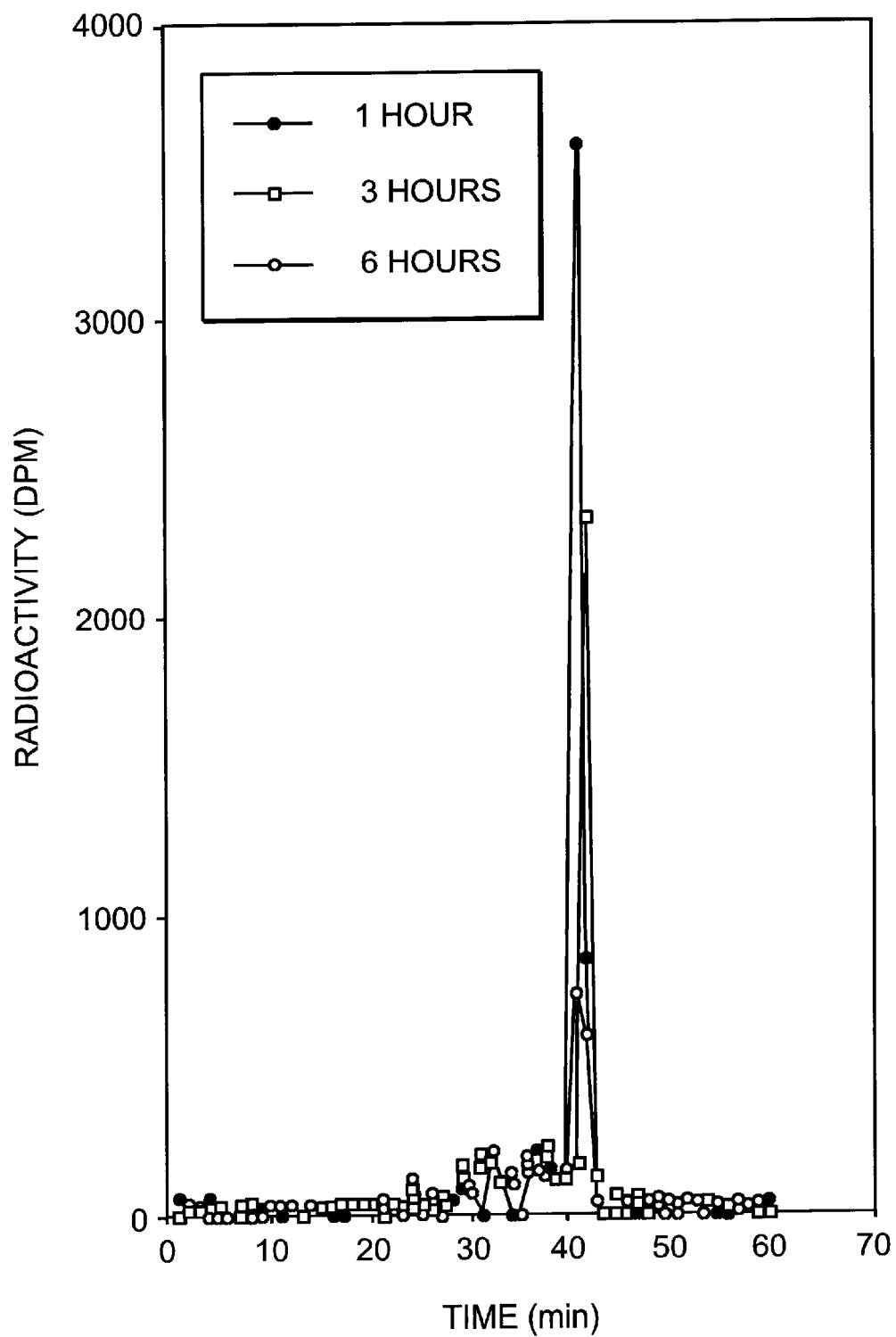
FIG. 9 is an HPLC chromatogram of oligonucleotides extracted from rat stomach 1 hour, 3 hours, and 6 hours after the administration of radiolabelled PS oligonucleotide.
Figure 10:
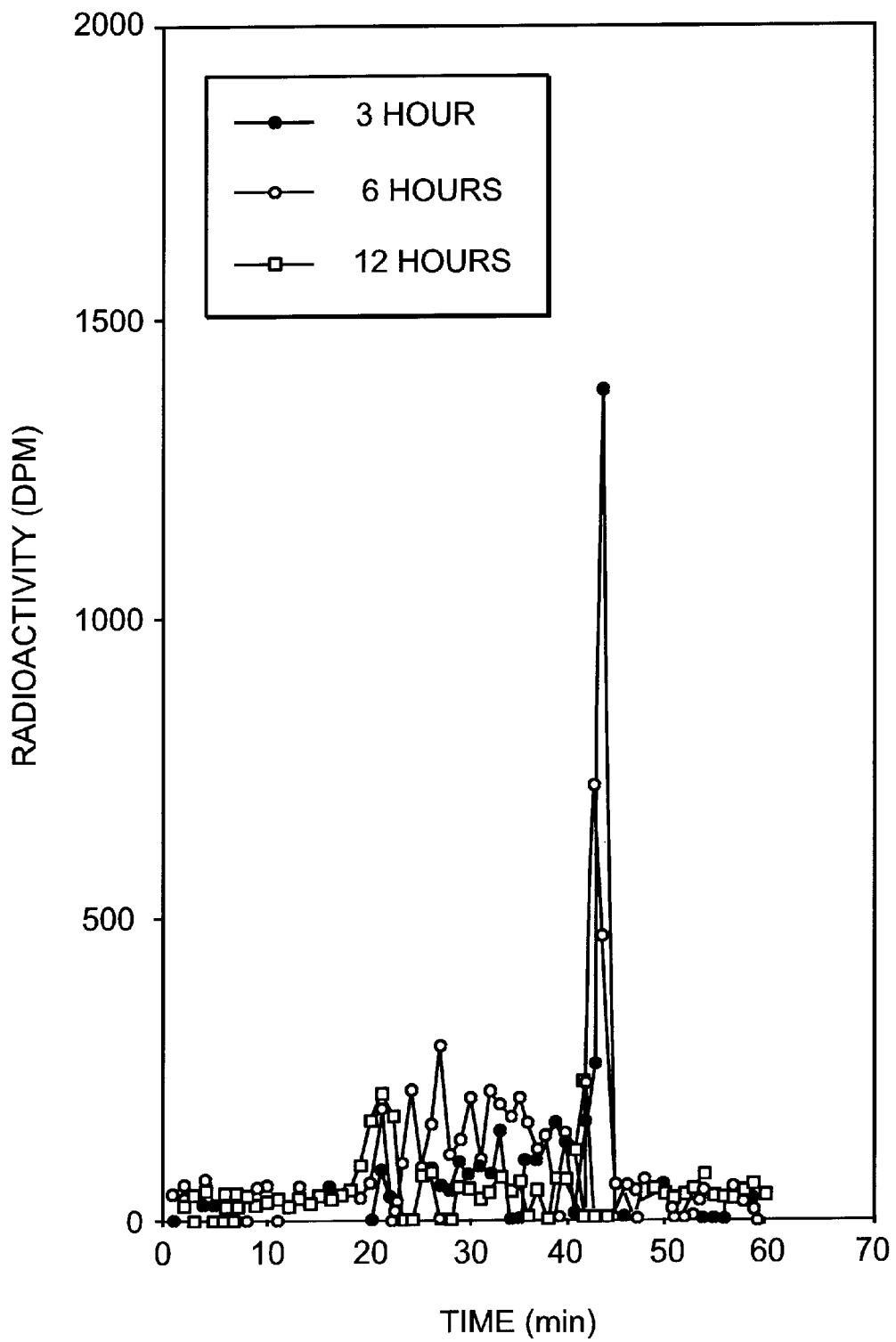
FIG. 10 is an HPLC chromatogram of oligonucleotides extracted from rat large intestine 3 hours, 6 hours, and 12 hours after the administration of radiolabelled PS oligonucleotide.

To determine the level of bioavailability of oligonucleotides following oral administration, the level of the oligonucleotide in the gastrointestinal tract (stomach and intestine) and feces was measured. FIG. 8 shows that approximately 80% of administered oligonucleotide remained or was excreted in feces, indicating that 20% of administered oligonucleotide was absorbed. This oligonucleotide was stable in stomach; no significant degradative products in stomach contents were detected six hours after oral administration (FIG. 9). The majority of administered oligonucleotide in the contents of the large intestine were also present as the intact compound (FIG. 10).

In another study, the oral bioavailability of unmodified, hybrid, and chimeric oligonucleotide administered to rat and mouse were compared, based on the quantitation of radioactivity in the gastrointestinal tract, feces, plasma, urine and remaining tissues at various times. Total recovery of radioactivity in the study was 92±6%. The total absorption of unmodified oligonucleotide was shown to be 17.3±5.5% over 6 hr and 35.5±6.0% over 12 hr following oral administration of the radiolabelled unmodified oligonucleotide to rats at a dose of 30 mg/kg. Minimal intact unmodified oligonucleotide was also detected in tissues outside enterohepatic system.

Figure 12:
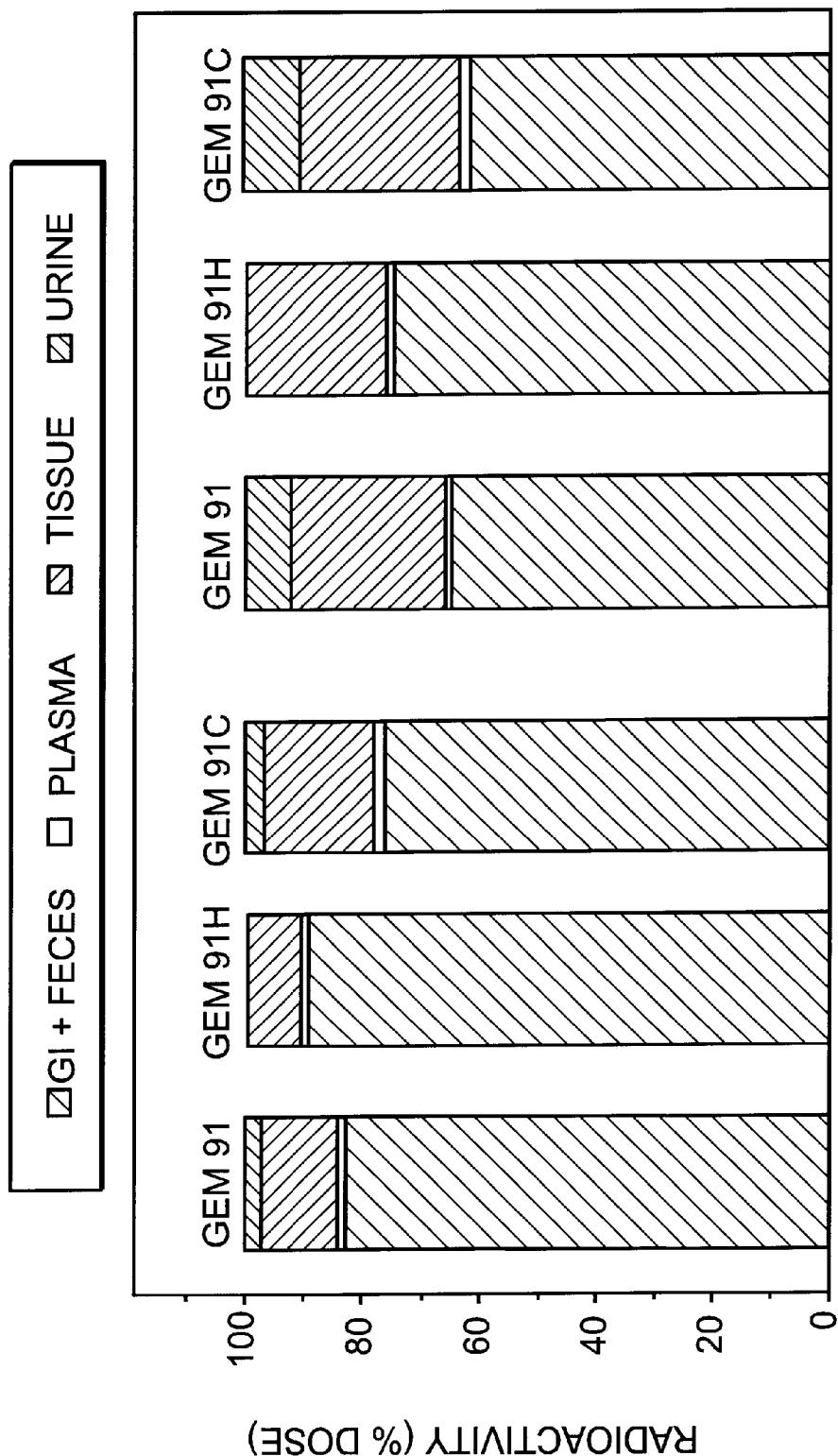
FIG. 12 is a graphic representation of the distribution of radioactivity in GI+feces, plasma, tissue, and urine at various times following oral administration of PS oligonucleotide (30 mg/kg rat), hybrid oligonucleotide (10 mg/kg mouse), and chimeric oligonucleotide (10 mg/kg mouse).

The total absorption of hybrid oligonucleotide was determined to be 10.2±2.5% over 6 hr and 25.9±4.7% over 12 hr following oral administration of the radiolabelled hybrid oligonucleotide in rats. Although the total absorption rates were slightly lower than that of the PS oligonucleotide, the hybrid oligonucleotide-derived radioactivity was stable in various tissues. The total absorption of the chimeric oligonucleotide was determined to be 23.6±2.8% over 6 hr and 39.3±2.4% over 12 hr following oral administration of the radiolabelled oligonucleotide. The comparison of oral availability of the three types of oligonucleotides is shown in FIG. 12, expressed as the percentages of administered doses in the gastrointestinal tract plus feces, in plasma, in tissues, and in urine.

Oral absorption of oligonucleotides in fasting animals was also determined with PS-oligonucleotide and hybrid oligonucleotide. Decreased absorption rates were found, indicating that the retention time of the oligonucleotides in the gastrointestinal tract in the fasting animals may be lower than in non-fasting animals.

These studies indicate that hybrid and chimeric oligonucleotides have enhanced bioavailability, which is associated with their stability in the gastrointestinal tract and other tissues.

Thus, using the method of the invention, successful absorption of oligonucleotides was accomplished through the gastrointestinal tract and distributed throughout the body. Intact oligonucleotides were detected in plasma and various tissues and excreted into the urine. These results demonstrate that oral administration is a potential means for delivery of oligonucleotides as therapeutic agents.

The following examples illustrate the preferred modes of making and practicing the present invention, but are not meant to limit the scope of the invention since alternative methods may be utilized to obtain similar results.

EXAMPLES

1. Synthesis and Analysis of Oligonucleotides

An unmodified HIV-specific 25mer oligonucleotide and hybrid 25mer phosphorothioate-linked oligonucleotide having SEQ ID NO:10 and containing 2'-O-methyl ribonucleotide 3' and 5' sequences and a deoxyribonucleotide interior, as well as two hybrid 18mer phosphorothioate-linked oligonucleotides having SEQ ID NOS:20 and 21, and containing 2'-O-methyl ribonucleotide 3' and 5' sequences and a deoxyribonucleotide interior, were synthesized, purified, and analyzed as follows.

Unmodified phosphorothioate deoxynucleosides were synthesized on CPG on a 5–6 μmole scale on an automated synthesizer (model 8700, Millipore, Bedford, Mass.) using the H-phosphonate approach described in U.S. Pat. No. 5,149,798. Deoxynucleoside H-phosphonates were obtained from Millipore (Bedford, Mass.). 2'-O-methyl ribonucleotide H-phosphonates or phosphorothioates were synthesized by standard procedures (see, e.g., "Protocols for Oligonucleotides and Analogs" in *Meth. Mol Biol.* (1993) volume 20) or commercially obtained (e.g., from Glenn Research, Sterling, Va. and Clontech, Palo Alto, Calif.). Segments of oligonucleotides containing 2'-O-methyl nucleoside(s) were assembled by using 2'-O-methyl ribonucleoside H-phosphonates or phosphorothioates for the desired cycles. Similarly, segments of oligonucleotides containing deoxyribonucleosides were assembled by using deoxynucleoside H-phosphonates for the desired cycles. After assembly, CPG bound oligonucleotide H-phosphonate was oxidized with sulfur to generate the phosphorothioate linkage. Oligonucleotides were then deprotected in concentrated NH$_4$OH at 40° C. for 48 hours.

Crude oligonucleotide (about 500 A$_{260}$ units) was analyzed on reverse low pressure chromatography on a C$_{18}$ reversed phase medium. The DMT group was removed by treatment with 80% aqueous acetic acid, then the oligonucleotides were dialyzed against distilled water and lyophilized.

Chimeric oligonucleotide was prepared as described in Zhang et al. (*J. Pharmacol. Exptal. Thera.* (1996) 278:(in press)). This chimeric oligonucleotide had 3 methylphosphate internucleotide linkages at its 5' end, 4 methylphosphonate internucleotide linkages at its 3' end, and phosphorothioate internucleotide linkages elsewhere in the molecule were prepared and purified as follows. The first four couplings were carried out by using nucleoside methylphosphoramidite, followed by oxidation with a standard iodine reagent. The next seven couplings were carried out by using nucleoside β-cyanoethylphosphoramidite, followed by oxidation with 3H-1,2-benzodithiole-3-one-1,1,-dioxide. The eighth coupling was carried out by using nucleoside β-cyanoethylphosphoramidite. After several washes with acetonitrile, the column was removed from the machine, and CPG-bound oligonucleotide was removed from the column and placed in an Eppendorf tube (1.5 ml).

2. Radioactive Labelling of Oligonucleotide

To obtain $^{35}$S-labelled oligonucleotide, synthesis was carried out in two steps. The first 19 nucleotides of the sequence SEQ ID NO:1) from its 3'-end were assembled using the β-cyanoethyl-phosphoramidite approach (see, Beaucage in *Protocols for Oligonucleotides and Analogs* (Agrawal, ed.), Humana Press, (1993), pp. 33–61). The last six nucleotides were assembled using the H-phosphonate approach (see, Froehler in *Protocols for Oligonucleotides and Analogs* (Agrawal, ed.) Humana Press, 1993, pp. 63–80). Controlled pore glass (CPG) support-bound oligonucleotide (30 mg of CPG; approximately 1 μM) containing five H-phosphonate linkage was oxidized with $^{35}$S$_8$ (4 mCi, 1 Ci/mg, Amersham; 1 Ci=37 GBq) in 60 ml carbon disulfide/pyridine/triethylamine (10:10:1). The oxidation reaction was performed at room temperature for 1 hr with occasional shaking. Then 2 μl, 5 μl, and 200 μl of 5% cold sulfur ($^{32}$S$_8$) in same solvent mixture was added every 30 min to complete the oxidation. The solution was removed and the CPG support was washed with carbon disulfide/pyridine/triethylamine (10:10:1) (3×500 μl) and with acetonitrile (3×700 μl). The product was deprotected in concentrated ammonium hydroxide (55° C., 14 hr) and evaporated. The resultant product was purified by polyacrylamide gel electrophoresis (20% polyacrylamide containing 7 M urea). The desired band was excised under UV shadowing and the PS-oligonucleotide was extracted from the gel and desalted with a Sep-Pak C18 cartridge (Waters) and Sephadex G-15 column. The yield was 20 A$_{260}$ units (600 μg; specific activity, 1 μCi/μg).

To prepare $^{35}$S-labelled chimeric oligonucleotide, CPG-bound oligonucleotide was treated with a mixture of elemental $^{35}$S (4.5 mCi/mg atom, in 50 μl of toluene; Amersham) in a solution of carbon disulfide, pyridine and triethylamine (200 μl, 200 μl and 4 μl, respectively) at 25° C. for 1 hr. 3H-1,2-benzodithiole-3-one-1,1-dioxide (1 ml, 2% in acetonitrile) was added, and the reaction mixture was allowed to remain at 25° C. for 10 min. The supernatant was removed and the CPG-bound oligonucleotide was washed with CH$_3$CN (10×1 ml). After capping with acetic anhydride (300 μl, tetrahydrofuran-lutidine-acetic anhydride, 8:1:1) and dimethylaminopyridine (300 μl, 0.625% in pyridine), the $^{35}$S-CPG-bound oligonucleotide was washed with acetonitrile (10×1 ml) and packed in the column. For the next eight couplings, we used nucleoside β-cyanoethylphosphoramidite followed by oxidation with 3H-1,2-benzodithiole-3-one-1,1-dioxide. The last four couplings were carried out by using nucleoside methylphosphonamidite followed by oxidation with iodine reagent. The crude CPG-bound 25mer chimeric oligonucleotide was treated with concentrated ammonium hydroxide (28%, 3 ml) at 25° C. for 2 hr. Evaporation on a Speed-Vac concentrator yielded a dried yellow pellet as crude $^{35}$S-labelled chimeric PS-oligonucleotide, which was immediately treated with a solution of ethylenediamine-ethanol-water (50:45:5, v/v/v/, 4 ml) for 4.5 hr at 25° C. Purification by PAGE (20% polyacrylamide, 7 M urea) gave pure $^{35}$S-labeled chimeric oligonucleotide as a white pellet (194 A$_{260}$ units, 155 μCi, 180 μCi/mol). Other chemicals and reagents used. in the present study were of the highest grade available.

3. Animals and Treatment

Male Sprague-Dawley rats (110+/−10 g, Harlan Laboratories, Indianapolis, Ind.) and male CD-/F2 mice (25 i 3 g, Charles River Laboratory, Wilmington, Mass.) were used in the study. The animals were fed with commercial diet and water ad libitum for 1 week prior to the study.

Unlabelled and $^{35}$S-labelled oligonucleotides were dissolved in physiological saline (0.9% NaCl) in a concentration of 25 mg/ml, and were administered to the fasted animals via gavage at the designated dose (30–50 mg/kg for rats and 10 mg/kg for mice). Doses were based on the pretreatment body weight and rounded to the nearest 0.01 ml. After dosing, each animal was placed in a metabolism cage and fed with commercial diet and water adlibitum. Total voided urine was collected and each metabolism cage was then washed following the collection intervals. Total excreted feces was collected from each animal at various timepoints, and feces samples were homogenized prior to quantitation of radioactivity. Blood samples were collected in heparinized tubes from animals at the various timepoints. Plasma was separated by centrifugation. Animals were euthanized by exsanguination under sodium pentobarbital anesthesia at various times (i.e., 1, 3, 6, 12, 24, and 48 hr; 3 animals/time point). Following euthanasia, the tissues were collected from each animal. All tissues/organs were trimmed of extraneous fat or connective tissue, emptied and cleaned of all contents, individually weighed, and the weights recorded prior to homogenization.

To quantitate the total absorption of the hybrid oligonucleotide, two additional groups of animals (3 per group) for each test oligonucleotide were treated using the same procedure as above. Animals were killed at 6 or 12 hr post dosing,. and the gastrointestinal tract was then removed. Radioactivities in the gastrointestinal tract, feces, urine, plasma, and the remainder of the body were determined separately. Total recovery of radioactivity was also determined to be 95±6%. The percentage of the absorbed hybrid oligonucleotide-derived radioactivity was determined by the following calculation:

$$\frac{\text{(total radioactivity in the remainder of the body} + \text{total radioactivity in urine)}}{\text{(total radioactivity in the gastrointestinal tract, feces, urine, plasma, and the remainder of the body)}} \times 100\%$$

4. Total Radioactivity Measurements

The total radioactivities in tissues and body fluids were determined by liquid scintillation spectrometry (LS 6000TA, Beckman, Irvine, Calif.). In brief, biological fluids (plasma, 50–100 µl; urine, 50–100 µl ) were mixed with 6 ml scintillation solvent (Budget-Solve, RPI, Mt. Prospect, Ill.) to determine total radioactivity. Feces were ground and weighed prior to being homogenized in a 9-fold volume of 0.9% NaCl saline. An aliquot of the homogenate (100 µl) was mixed with solubilizer (TS-2, RPI, Mt. Prospect, Ill.) and then with scintillation solvent (6 ml) to permit quantitation of total radioactivity.

Following their removal, tissues were immediately blotted on Whatman No. 1 filter paper and weighed prior to being homogenized in 0.9% NaCl saline (3–5 ml per gram of wet weight). The resulting homogenate (100 µl) was mixed with solubilizer (TS-2, RPI, Mt. Prospect, Ill.) and then with scintillation solvent (6 ml) to determine total radioactivity. The volume of 0.9% NaCl saline added to each tissue sample was recorded. The homogenized tissues/organs were kept frozen at $\leq -70°$ C. until the use for further analysis.

5. HPLC Analysis

The radioactivity in urine was analyzed by paired-ion HPLC using a modification of the method described essentially by Sands et al. (*Mol. Pharm.* (1994) 45:932–943). Urine samples were centrifuged and passed through a 0.2-µm Acro filter (Gelman, Ann Arbor, Mich.) prior to analysis. Hybrid oligonucleotide and metabolites in plasma samples were extracted using the above methods in sample preparation for PAGE. A Microsorb MV-C4 column (Rainin Instruments, Woburn, Mass.) was employed in HPLC using a Hewlett Packard 1050 HPLC with a quaternary pump for gradient making. Mobile phase included two buffers; Buffer A was 5 mM-A reagent (Waters Co., Bedford, Mass.) in water and Buffer B was 4:1 (v/v) Acetonitrile (Fisher)/water. The column was eluted at a flow rate of 1.5 ml/min, using the following gradient: (1) 0–4 min, 0% buffer B; (2) 4–15 min 0–35% Buffer B; and (3) 15–70 min 35%-80% Buffer B. The column was equilibrated with Buffer A for at least 30 min prior to the next run. By using a RediFrac fraction collector (Pharmacia LKB Biotechnology, Piscataway, N.J.), 1-min fractions (1.5 ml) were collected into 7-ml scintillation vials and mixed with 5 ml scintillation solvent to determine radioactivity in each fraction.

6. PAGE and Autoradiography

Plasma and tissue homogenates were incubated with proteinase K (2 mg/ml) in extraction buffer (0.5% SDS/10 mM NaCl/20 mM Tris-HCl, pH 7.6/10 mM EDTA) for 1 hr at 60° C. The samples were then extracted twice with phenol/chloroform (1:1, v/v) and once with chloroform. After ethanol precipitation, the extracts were analyzed by electrophoresis in 20% polyacrylamide gels containing 7 M urea. Urine samples were filtered, desalted and then analyzed by polyacrylamide gel electrophoresis (PAGE). The gels were fixed in 10% acetic acid/10% methanol solution and then dried before autoradiography.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for introducing an intact oligonucleotide into a mammal, comprising the step of orally administering an oligonucleotide of about 15 to 30 nucleotides, the oligonucleotide comprising phosphorothioate internucleoside linkages between adjacent nucleosides and further comprising at least one 2'-O-alkoxyalkyl-ribonucleotide at each end, whereby the oligonucleotide is present in intact form in liver and kidney tissue of the mammal following oral administration.

2. The method of claim 1, wherein the 2'-O-alkoxyalkyl ribonucleotide is a 2'-O-methoxyethyl-ribonucleotide.

* * * * *

UNITED STATES PATENT AND TRADEMARK OFFICE
CERTIFICATE OF CORRECTION

PATENT NO. : 6,608,035 B1  
DATED : August 19, 2003  
INVENTOR(S) : Sudhir Agrawal et al.

It is certified that error appears in the above-identified patent and that said Letters Patent is hereby corrected as shown below:

Title page,
Item [56], References Cited, OTHER PUBLICATIONS,
"Agwaral et al." reference, please delete "(Agwaral)" and insert therefor -- (Agrawal) --;
"Agrawal" reference, please delete "Ed." and insert therefor -- Eds. --.

Signed and Sealed this

Second Day of August, 2005

JON W. DUDAS
*Director of the United States Patent and Trademark Office*